(12) United States Patent
Anderson et al.

(10) Patent No.: US 8,206,281 B2
(45) Date of Patent: Jun. 26, 2012

(54) METHOD AND APPARATUS FOR TREATING PELVIC ORGAN PROLAPSE

(75) Inventors: Kimberly A. Anderson, Eagan, MN (US); James E. Cox, Corcoran, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 12/855,792

(22) Filed: Aug. 13, 2010

(65) Prior Publication Data
US 2011/0015479 A1 Jan. 20, 2011

Related U.S. Application Data

(60) Division of application No. 11/518,932, filed on Sep. 12, 2006, now Pat. No. 7,811,222, and a continuation-in-part of application No. 10/834,943, filed on Apr. 30, 2004, now Pat. No. 7,500,945, and a continuation-in-part of application No. 10/840,646, filed on May 7, 2004, now Pat. No. 7,351,197.

(60) Provisional application No. 60/716,110, filed on Sep. 12, 2005.

(51) Int. Cl.
*A61F 2/00* (2006.01)
(52) U.S. Cl. ............... 600/37; 600/29; 600/30
(58) Field of Classification Search ............ 600/29–32, 600/37; 606/1, 99, 104, 119, 139, 159, 190, 606/222–227
See application file for complete search history.

(56) References Cited

U.S. PATENT DOCUMENTS

| | | | |
|---|---|---|---|
| 2,738,790 | A | 3/1956 | Todt et al. |
| 3,124,136 | A | 3/1964 | Usher |
| 3,182,662 | A | 5/1965 | Shlrodkar |
| 3,311,110 | A | 3/1967 | Singerman at al. |
| 3,384,073 | A | 5/1968 | Van Winkle, Jr. |

(Continued)

FOREIGN PATENT DOCUMENTS
DE 23 05 815 A1 8/1974
(Continued)

OTHER PUBLICATIONS

"Urinary Incontinence: Easier Operation" Article from La Libre Belgique, Wednesday, Oct. 15, 2003 (English translation provided).

(Continued)

*Primary Examiner* — Charles A Marmor, II
*Assistant Examiner* — Carrie R Dorna
(74) *Attorney, Agent, or Firm* — Kimberly K. Baxter; Gregory L. Koeller

(57) ABSTRACT

An apparatus for treating pelvic organ prolapse in a patient is provided. The apparatus includes a support portion having first and second ends. A first elongated end portion is connected to said first end of said support portion. The first elongated end portion includes a first dilator configured to attach securely with a tip of a needle. A second elongated end portion is connected to said second end of said support portion. The second elongated end portion includes a second dilator configured to attach securely with a tip of a needle. The first and second needles include a straight portion, a tip, a first radius, and a second radius distinct from the first radius. The first radius and the second radius are disposed between the straight portion and the tip. A method and kit for said treatment is further provided.

21 Claims, 19 Drawing Sheets

U.S. PATENT DOCUMENTS

| | | |
|---|---|---|
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,204,541 A | 5/1980 | Kapitanov |
| 4,235,238 A | 11/1980 | Ogiu et al. |
| 4,246,660 A | 1/1981 | Wevers |
| 4,265,231 A | 5/1981 | Scheller, Jr. et al. |
| 4,441,497 A | 4/1984 | Paudler |
| 4,509,516 A | 4/1985 | Richmond |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,920,986 A | 5/1990 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,188,636 A | 2/1993 | Fedotov |
| 5,207,694 A | 5/1993 | Broome |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,520,703 A | 5/1996 | Essig et al. |
| 5,544,664 A | 8/1996 | Benderev et al. |
| 5,562,685 A | 10/1996 | Mollenauer et al. |
| 5,562,689 A | 10/1996 | Green et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,662,683 A | 9/1997 | Kay |
| 5,669,935 A | 9/1997 | Rosenman et al. |
| 5,683,349 A | 11/1997 | Makower et al. |
| 5,807,403 A | 9/1998 | Beyar et al. |
| 5,810,882 A | 9/1998 | Bolduc et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,904,696 A | 5/1999 | Rosenman |
| 5,919,232 A | 7/1999 | Chaffringeon et al. |
| 5,934,283 A | 8/1999 | Willem et al. |
| 5,935,122 A | 8/1999 | Fourkas et al. |
| 5,935,138 A | 8/1999 | McJames, II et al. |
| 5,944,732 A | 8/1999 | Raulerson et al. |
| 5,972,000 A | 10/1999 | Beyar et al. |
| 5,988,171 A | 11/1999 | Sohn et al. |
| 5,992,269 A | 11/1999 | Puig et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,042,534 A | 3/2000 | Gellman et al. |
| 6,042,536 A | 3/2000 | Tihon et al. |
| 6,048,351 A | 4/2000 | Gordon et al. |
| 6,050,937 A | 4/2000 | Benderev |
| 6,053,935 A | 4/2000 | Brenneman et al. |
| 6,068,591 A | 5/2000 | Bruckner et al. |
| 6,071,290 A | 6/2000 | Compton |
| 6,099,538 A | 8/2000 | Moses et al. |
| 6,106,545 A | 8/2000 | Egan |
| 6,110,101 A | 8/2000 | Tihon et al. |
| 6,117,067 A | 9/2000 | Gil-Vernet |
| 6,168,611 B1 | 1/2001 | Risvi |
| 6,221,005 B1 | 4/2001 | Bruckner et al. |
| 6,273,852 B1 | 8/2001 | Lehe et al. |
| 6,302,840 B1 | 10/2001 | Benderev |
| 6,306,079 B1 | 10/2001 | Trabucco |
| 6,328,744 B1 | 12/2001 | Harari et al. |
| 6,334,446 B1 | 1/2002 | Beyar |
| 6,352,553 B1 | 3/2002 | van de Burg et al. |
| 6,367,353 B2 | 4/2002 | Puig et al. |
| 6,382,214 B1 | 5/2002 | Raz et al. |
| 6,406,423 B1 | 6/2002 | Scetbon |
| 6,406,480 B1 | 6/2002 | Beyar et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,494,906 B1 | 12/2002 | Owens |
| 6,502,578 B2 | 1/2003 | Raz et al. |
| 6,530,943 B1 | 3/2003 | Hoepffner et al. |
| 6,582,443 B2 | 6/2003 | Cabak et al. |
| 6,626,917 B1 | 9/2003 | Craig |
| 6,663,633 B1 | 12/2003 | Pierson, II |
| 6,911,003 B2 | 6/2005 | Anderson et al. |
| 7,094,199 B2 | 8/2006 | Petros et al. |
| 2001/0000533 A1 | 4/2001 | Kovac |
| 2001/0049467 A1 | 12/2001 | Lehe et al. |
| 2002/0022841 A1 | 2/2002 | Kovac |
| 2002/0028980 A1 | 3/2002 | Thierfelder et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslaine et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0165566 A1 | 11/2002 | Ulmsten |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023137 A1 | 1/2003 | Gellman |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0045892 A1 | 3/2003 | Kaladelfos |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0100954 A1 | 5/2003 | Schuldt-Hempe et al. |
| 2003/0114866 A1 | 6/2003 | Ulmsten et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0191480 A1 | 10/2003 | Ulmsten et al. |
| 2003/0199732 A1 | 10/2003 | Suslian et al. |
| 2003/0220538 A1 | 11/2003 | Jacquetin |

| | | | |
|---|---|---|---|
| 2004/0039246 | A1 | 2/2004 | Gellman et al. |
| 2004/0039453 | A1 | 2/2004 | Anderson et al. |
| 2004/0116774 | A1 | 6/2004 | Migliari |
| 2004/0144395 | A1 | 7/2004 | Evans et al. |
| 2004/0249473 | A1* | 12/2004 | Delorme et al. ........... 623/23.64 |
| 2005/0004426 | A1 | 1/2005 | Raz et al. |
| 2005/0065395 | A1 | 3/2005 | Mellier |

FOREIGN PATENT DOCUMENTS

| | | |
|---|---|---|
| DE | 42 20 283 C2 | 12/1993 |
| DE | 43 04 353 A1 | 4/1994 |
| DE | 101 38 950 A1 | 2/2003 |
| DE | 102 11 360 A1 | 10/2003 |
| EP | 0 470 308 A1 | 2/1992 |
| EP | 0 643 945 A2 | 3/1995 |
| EP | 0 650 703 A1 | 5/1995 |
| EP | 1 093 768 A1 | 4/2001 |
| SU | 1225547 A | 4/1986 |
| SU | 1342486 A1 | 10/1987 |
| WO | WO 93/17635 A1 | 9/1993 |
| WO | WO 93/19678 A2 | 10/1993 |
| WO | WO 97/16121 A1 | 5/1997 |
| WO | WO 98/19606 A1 | 5/1998 |
| WO | WO 98/35606 A2 | 8/1998 |
| WO | WO 98/35616 A1 | 8/1998 |
| WO | WO 98/35632 A | 8/1998 |
| WO | WO 98/35632 A1 | 8/1998 |
| WO | WO 99/52450 A1 | 10/1999 |
| WO | WO 00/13601 A1 | 3/2000 |
| WO | WO 00/18319 A1 | 4/2000 |
| WO | WO 00/57812 A1 | 10/2000 |
| WO | WO 00/64370 A1 | 11/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/39670 A1 | 6/2001 |
| WO | WO 01/45589 A1 | 6/2001 |
| WO | WO 01/56499 A1 | 8/2001 |
| WO | WO 01/78609 A2 | 10/2001 |
| WO | WO 02/02031 A1 | 1/2002 |
| WO | WO 02/19944 A2 | 3/2002 |
| WO | WO 02/26108 A2 | 4/2002 |
| WO | WO 02/28312 A1 | 4/2002 |
| WO | WO 02/32284 A2 | 4/2002 |
| WO | WO 02/34124 A2 | 5/2002 |
| WO | WO 02/38079 A2 | 5/2002 |
| WO | WO 02/39890 A2 | 5/2002 |
| WO | WO 02/069781 A2 | 9/2002 |
| WO | WO 02/071953 A2 | 9/2002 |
| WO | WO 02/078552 A1 | 10/2002 |
| WO | WO03/096929 | 11/2003 |
| WO | WO 2004/016196 A2 | 2/2004 |
| WO | WO2004/017862 | 3/2004 |
| WO | WO 2004/019786 A1 | 3/2004 |

OTHER PUBLICATIONS

Aldridge, Albert H., B.S., M.D., F.A.C.S., "Transplantation of Fascia for Relief of Urinary Stress incontinence" Am. J. of Obstet. and Gynec., vol. 44, pp. 398-411 (1948).
Arakl, Tohru, et al. "The Loop-Loosening Procedure for Urination Difficulties After Stamey Suspension of the Vesical Neck" The Journal of Urology, vol. 144, pp. 319-323, (Aug. 1990) American Urological Association, Inc.
Asmussen, M., et al., "Simultaneous Urethro-Cystometry With a New Technique" Scand J Urol Nephrol 10, pp. 7 11 (1976).
Beck, Peter R. et al., "Treatment of Urinary Stress Incontinence With Anterior Colporrhaphy" Obstetrics and Gynecology, vol. 59 (No. 3), pp. 269-274 (Mar. 1982).
Benderev, Theodore V., M.D., "Anchor Fixation and Other Modifications of Endoscopic Bladder Neck Suspension" Urology, vol. 40, No. 5, pp. 409-418 (Nov. 1992).
Benderev, Theodore V., MD, "A Modified Percutaneous Outpatient Bladder Neck Suspension System" Journal of Urology, vol. 152, pp. 2316-2320 (Dec. 1994).

Bergman, Arieh, M.D. et al., "Three surgical procedures for genuine stress incontinence; Five-year follow-up of a prospective randomized study" Am. J. Obstet Gynecol, vol. 173 No. 1, pp. 66-71 (Jul. 1995).
Blaivas, Jerry G., "Commentary: Pubovaginal Sling Procedure" Surgery for Female Urinary Incontinence, pp. 93-101 (1990).
Blaivas, Jerry G., et al., "Pubovaginal Fascial Sling for the Treatment of Complicated Stress Urinary Incontinence" The Journal of Urology, vol. 145, pp. 1214-1218 (Jun. 1991) American Urological Association, Inc.
Blaivas, Jerry G., M.D., et al., "Type III Stress Urinary Incontinence: Importance of Proper Diagnosis and Treatment" Gynecology and Obstetrics Surgical Forum , 35, pp. 473-475 (1984).
Bryans, Fred E., M.D., F.R.C.S.(C.),"Marfex gauze hammock sling operation with Cooper's ligament attachment in the management of recurrent urinary stress incontinence" Am. J. Obstet. Gynecol., col. 133, No. 3, pp. 292-294 (Feb. 1, 1979).
Burch, John C., M.D., "Urethrovaginal fixation to Cooper's ligament for correction of stress incontinence, cystocele, and prolapse" Am. J. Obstet & Gynecol., vol. 81 No. 2, pp. 281-290 (Feb. 1961).
Choe, Jong M., et al., "Gore-Tex Patch Sling: 7 Years Later" Urology, 54 (4) pp. 641-646 (1999) Elsevier Science Inc.
Chu, C.C., and Welch, L., "Characterization of Morphologic and Mechanical Properties of Surgical Mesh Fabrics" Journal of Biomedical Materials Research, vol. 19, pp. 903-916 (1985) © 1985 John Wiley & Sons, Inc.
Dargent, D., et al. Pose d'un ruban sous uretral oblique par voie obturatrice dans le traitement de l'incontinence urinaire feminine, Gynecol Obstet Fertil 2002; 30: pp. 576-782 (2002) (English translation provided).
Das, Saktl et al., "Laparoscopic Colpo-Suspension" The Journal of Urology, vol. 154, pp. 1119-1121 (Sep. 1995).
de Leval, Jean "Novel Surgical Technique for the Treatment of Female Stress Urinary Incontinence: Transobturator Vaginal Tape Inside-Out" European Urology 44 pp. 724-730 (2003).
Decter, Ross M., "Use of the Fascial Sling for Neurogenic Incontinence: Lessons Learned" The Journal of Urology, vol. 150, pp. 683-686, (Aug. 1993) American Urological Association, Inc.
DeLancey, John O. L., M.D., "Structural support of the urethra as It relates to stress urinary incontinence: The hammock hypothesis" Am. J Obstet Gynecol, pp. 1713-1723 (Jun. 1994).
Delorme, "La bandelette trans-obturatrice: un procede mini-invasil pour traiter l'Incontinence urinalre d'effort de la femme", Urologie de la Femme, Progres en Urologie (2001), 11, 1306-1313 (Sep. 2001) (English translation provided).
Delorme, Emmanuel et al., "Transobturator Tape (Uratape®): A New Minimally-Invasive Procedure to Treat Female Urinary Incontinence" European Urology 45 (2004) 203-207 (Dec. 2003).
Dietz, H.P., et al., "Mechanical Properties of urogynecologic Implant Materials" International Urogynecology Journal (2003) 14:239-243 (Aug. 5, 2003).
Enzelsberger, H., et al., "Urodynamic and Radlologic Parameters Before and After Loop Surgery for Recurrent Urinary Stress Incontinence" Acta Obstet Gynecol Scand 1990; 69 pp. 51-54 (1990).
Eriksen, Bjame C., et al., "Long-Term Effectiveness of the Burch Colposuspension in Female Urinary Stress Incontinence" Acta Obstet Gynecol Scand 1990; 69 pp. 45-50 (1990).
Falconer, C. et al., "Clinical Outcome and Changes in Connective Tissue Metabolism After Intravaginal Slingplasty in Stress Incontinent Women" International Urogynecol J, vol. 7, pp. 133-137, (1996).
Falconer, C., et al., "Influence of Different Sling Materials on Connective Tissue Metabolism in Stress Urinary Incontinent Women" International Urogynecolcgy Journal, (2001) (Supp. 2) pp. S19-S23 (2001).
Gilja, Ivan et all, "A Modified Raz Bladder Neck Suspension Operation (Transvaginal Burch)" The Journal of Urology, vol. 153, pp. 1455-1457 (May 1995).
Gittes, Ruben F., et al, "No-Incision Pubovaginal Suspension for Stress Incontinence" The Journal of Urology, vol. 138, pp. 568-570 (Sep. 1987).
Handa, Victoria L., M.D. et al., "Banked Human Fascia Lata for the Suburethral Sling Procedure: A Preliminary Report" Obstetrics and Gynecology, vol. 88, No. 6, pp. 1045-1049 (Dec. 1996).

Henriksson, L., M.D. et al., "A urodynamic evaluation of the effects of abdominal urethrocystopexy and vaginal sling urethroplasty in women with stress incontinence" Am. J. Obstet. Gynecol, pp. 77-82 (May 1, 1978).

Hershom, Sender, M.D. et al., "Gynecare TVT With Abdominal Guides Early Clinical Experience" Gynecare TVT, Marketing Material, Gynecare Worldwide (May 2002), 12 pages.

Hodgkinson, C. Paul, M.D., et al., "Urinary Stress Incontinence in the Female—III. Round-ligament technic for retropubic suspension of the urethra" Obstetrics and Gynecology, vol. 10, No. 5, pp. 493-499 (Nov. 1957).

Hohenfellner, Rudolf, et al., "Sling Procedures" Surgery of Female Incontinence—Second Edition, Chapter 7, pp. 105-113, Springer-Verlag (May 1, 1986).

Holschneider, C.H., et al., "The Modified Pereyra Procedure in Recurrent Stress Urinary Incontinence: A 15-year Review" Obstetrics & Gynecology, vol. 83, No. 4, pp. 573-578 (Apr. 1994).

Horbach, Nicollette S., "Suburethral Sling Procedures" Urolgynecology and Urodynamics Theory and Practice, Fourth Edition, Chapter 42, pp. 569-579, Williams & Wilkins (1996).

Horbach, Nicollette S., et al., "A Suburethral Sling Procedure with Polytetrafluoroethylene for the Treatment of Genuine Stress Incontinence in Patients with Low Urethral Closure Pressure" Obstetrics & Gynecology, vol. 71, No. 4, pp. 648-652 (Apr. 1988).

Iglesia, C.B., et al., "The Use of Mesh in Gynecologic Surgery" International Urogynecology Journal (1997) 8:105-115, Springer-Verlag London Ltd. (1997).

Ingelman-Sundberg, A., et al., "Surgical Treatment of Female Urinary Stress Incontinence" Contr. Gynec. Obstet. vol. 10, pp. 51-69 (Karger. Basel 1983).

Jeffcoate, T. N. A., M.D., F.R.C.S.E., F.R.C.O.G., "The Results of the Aldridge Sling Operation for Stress Incontinence" J Obstet Gynaecol Br Emp., 63(1) pp. 36-39 (Feb. 1956).

Karram, Mickey M., M.D. et al., "Patch Procedure: Modified Transvaginal Fascia Lala Sling for Recurrent or Severe Stress Urinary Incontinence" Obstetrics & Gynecology, vol. 75, No. 3, Part 1, pp. 461-463 (Mar. 1990).

Kersey, J., "The gauze hammock sling operation in the treatment of stress incontinence" British Journal of Obstetrics and Gynaecology, vol. 90 pp. 945-949, (Oct. 1983).

Klutke, Carl et al., "The Anatomy of Stress Incontinence: Magentic Resonance Imaging of the Female Bladder Neck and Urethra" The Journal of Urology, vol. 143, pp. 563-566 (Mar. 1990).

Klutke, John James et al., "Transvaginal Bladder Neck Suspension to Cooper's Ligament: A Modified Pereyra Procedure" Obstetrics & Gynecology, vol. 88, No. 2, pp. 294-298 (Aug. 1996).

Klutke, John, M.D. et al., "The promise of tension-free vaginal tape for female SUI" Contemporary Urology, pp. 59-60, 65-66, 69-70, 73 (Oct. 2000).

Korda, Andrew, et al., "Experience with Silastic Slings for Female Urinary Incontinence" Aust NZ J Obstet Gynaecol, vol. 29, pp. 150-154 (1989).

Kovac, S. Robert, et al, "Pubic Bone Suburethral Stabilization Sling for Recurrent Urinary Incontinence" Obstetrics & Gynecology, vol. 89, No. 4, pp. 624-627 (Apr. 1997).

Kovac, S. Robert, et al, "Pubic Bone Suburethral Stabilization Sling: A Long Term Cure for SUI?" Contemporary OB/GYN, 8 pages (Feb. 1998).

Kovac, S. Robert, "Follow-up of the Pubic Bone Suburethral Stabilization Sting Operation for Recurrent Urinary Incontinence (Kovac Procedure)" Journal of Pelvic Surgery, pp. 156-160 (May 1999).

Leach, Gary E., et al, "Female Stress Urinary Incontinence Clinical Guidelines Panel Report on Surgical Management of Female stress Urinary Incontinence" American Urological Association, vol. 158, pp. 875-880 (Sep. 1997).

Leach, Gary E., MD, "Bone Fixation Technique for Transvaginal Needle Suspension" Urology vol. XXXI, No. 5, pp. 388-390 (May 1988).

Letters to the Editor, R. Villet's response to the article by D. Dargent et al., "Placement of an oblique transobturator suburethral tape in the treatment of female urinary incontinence", Gynecology Obstetrics & Fertility 31, pp. 96-101 (2003) (English translation provided).

Lichtenstein, Irving L., M.D., et al., "The Tension-Free Hemloplasty" The American Journal of Surgery, vol. 157, pp. 188-193 (Feb. 1989).

Loughlin, Kevin R., et al., "Review of an 8-Year Experience With Modifications of Endoscopic Suspension of the Bladder Neck for Female Stress Urinary Incontinence" The Journal of Urology, vol. 143, pp. 44-45 (Jan. 1990).

Marshall, Victor Fray, M.D., F.A.C.S. et al., "The Correction of Stress Incontinence by Simple Vesicourethral Suspension" Surgery, Gynecology and Obstetrics, vol. 88, pp. 509-518 (1949).

Masclo, Valenzio C., M.D., "Therapy of Urinary Stress incontinence in Women Using Mitek GII Anchors" Mitek Surgical Products, Inc., 5 pages (1993).

McGuire, Edward J. et al., "Abdominal Fascial Slings" Female Urology 2nd ed. (Raz. S. ed.). W.B. Saunders Company, Chapter 31, pp. 369-375 (1996).

McGuire, Edward J. et al., "Experience With Pubovaginal Slings for Urinary Incontinence at the University of Michigan" The Journal of Urology, vol. 138, pp. 525-526 (Sep. 1987).

McGuire, Edward J., et al., "Pubovaginal Sling Procedure for Stress Incontinence" The Journal of Urology, vol. 119, pp. 82-84 (Jan. 1978) The Williams & Wilkins Co.

McGuire, Edward J., M.D., "Abdominal Procedures for Stress Incontinence" Symposium on Female Urology, Urologic Clinics of North America—vol. 12, No. 2, pp. 285-290 (May 1985).

McIndoe, G. A. J., et al., "The Aldridge Sling Procedure in the Treatment of Urinary Stress Incontinence" Aust NZ J Obstet Gynaecol, vol. 27, pp. 238-239 (1987).

McKiel, Charles F., Jr. et al., "Marshall-Marchetti Procedure: Modification" 1st Journal in Urology, vol. 96, pp. 737-739 (Nov. 1966) The Williams & Wilkins Co.

Moir, J. Chessar, "The Gauze-Hammock Operation (A Modified Aldridge Sling Prcedure)" The Journal of Obstetrics and Gynaecology of the British Commonwealth, vol. 75 No. 1, pp. 1-9 (Jan 1968).

Morgan, J.E., M.D. et al., "The Marlex Sling Operation for the Treatment of Recurrent Stress Urinary Incontinence: A 16-Year Review", Am. J. Obstet. Gynecol., vol. 151, No. 2, pp. 224-226 (Jan. 15, 1985).

Morgan, J.E., M.D., "A sling operation, using Marlex Polypropylene mesh, for treatment of recurrent stress incontinence", Amer. J. Obstet. Gynecol., vol. 106, No. 3, pp. 369-377 (Feb. 15, 1970).

Narik, G., M.D., "A simplified sling operation suitable for routine use" Am. J. Obst. & Gynec., vol. 84, No. 3, pp. 400-405 (Aug. 1, 1962).

Nichols, David H., MD, FACOG, "The Mersilene Mesh Gauze-Hammock for Severe Urinary Stress Incontinence" Obstetrics and Gynecology, vol. 41, No. 1, pp. 88-93 (Jan. 1973).

Nickel, Rafael F., et al., "Evaluation of a Transpelvic Sling Procedure With and Without Colposuspension for Treatment of Female Dogs With Refractory Urethral Sphincter Mechanism Incompetence" Veterinary Surgery, vol. 27, pp. 94-104, (1998), The American College of Veterinary Surgeons.

Norris, Jeffrey P., M.D., et al., "Use of Synthetic Material in Sling Surgery: A Minimally Invasive Approach" Journal of Endourology, vol. 10 No. 3, pp. 227-230 (Jun. 1996) Mary Ann Liebert, Inc.

O'Donnell, Pat D., M.D., "Combined Raz Urethral Suspension and McGuire Pubovaginal Sling for Treatment of Complicated Stress Urinary Incontinence" Journal of The Arkansas Medical Society, vol. 88, No. 8, pp. 389-392 (Jan. 1992).

Parra, R. O., et al., "Experience with a Simplified Technique for the Treatment of Female Stress Urinary Incontinence" British Journal of Urology, vol. 66, pp. 615-617 (1990).

Pelosi, Marco A., II, et al., "New Tranobturator Sling Reduces Risk of Injury" OBG Management, pp. 17-20, 30, 32, 35-38 (Jul. 2003).

Pelosi, Marco Antonio III et al., "Pubic Bone Suburethral Stabilization Sling: Laparoscopic Assessment of a Transvaginal Operation for the Treatment of Stress Urinary Incontinence" Journal of Laparoendoscopic & Advanced Surgical Techniques, vol. 9, No. 1 pp. 45-50 (1999).

Pereyra, Armand J. et al, "Pubourethral Supports in Perspective: Modified Pereyra Procedure for Urinary Incontinence" Obstetrics and Gynecology, vol. 59, No. 5, pp. 643-648 (May 1982).

Pereyra, Armand J., M.D., F.A.C.S., "A Simplified Surgical Procedure for the Correction of Stress Incontinence in Women" West J. Surg. Obst. & Gynec. pp. 223-226 (Jul.-Aug. 1959).

Petros, P. E. Papa, "Medium-term Follow-up of the Intravaginal Slingplasty Operation Indicates Minimal Deterioration of Urinary Continence With Time" Aust NZ J Obstet Gynaecol, vol. 39, No. 3, pp. 354-356 (1999) (International Urogynecology Journal and Pelvic Floor Dysfunction, Reprinted from vol. 7, No. 3, pp. 133-137 (1996)).

Petros, P. E. Papa, "New Ambulatory Surgical Methods Using an Anatomical Classification of Urinary Dysfunction Improve Stress, Urge and Abnormal Emptying" Int-Urogynecol-J-Pelvic-Floor-Dysfunct, 8/5, pp. 270-277 (1997).

Petros, P. E. Papa, et al., "An analysis of rapid pad testing and the history for the diagnosis of stress incontinence" Acta Obstet Gynecol Scand 71, pp. 529-536 (1992).

Petros, P. E. Papa, et al., "An Anatomical Basis for Success and Failure of Female Incontinence Surgery" Scand J Ural Nephrol, Suppl. No. 153, pp. 55-60 (1993).

Petros, P. E. Papa, et al., "An integral theory of female urinary incontinence—Experimental and clinical considerations" Acta Obstet Gynecol Scand, vol. 69, Suppl. 153, pp. 7-31 (1990), The Scandinavian Association of Obstetricians and Gynecologists.

Petros, P. E. Papa, et al., "Anchoring the midurethra restores bladder-neck anatomy and continence" The Lancet, vol. 354, pp. 997-998 (Sep. 18, 1999).

Petros, P. E. Papa, et al., "Bladder instability in Women: A Premature Activation of the Micturition Reflex" Neurourology and Urodynamics, vol. 12, pp. 235-238 (1993).

Petros, P. E. Papa, et al., "Cough Transmission Ratio: An Indicator of Suburethral Vaginal Wall Tension Rather Than Urethral Closure?" Acta Obstet Gynecol Scand, vol. 69 Suppl. 153, pp. 37-39 (1990).

Petros, P. E. Papa, et al., "Cure of Stress Incontinence by Repair of External Anal Spincter: Two Case Reports" Acta Obstet Gynecol Scand, vol. 69 Suppl. 153, p. 75 (1990).

Petros, P. E. Papa, et al., "Cure of Urge Incontinence by the Combined Intravaginal Sling and Tuck Operation" Acta Obstet Gynecol Scand, vol. 69 Suppl. 153, pp. 61-62 (1990).

Petros, P. E. Papa, et al., "Further Development of the Intravaginal Slingplasty Procedure—IVS III—(with midline "tuck")" Scand J Urol Nephrol, Suppl. 153, pp. 69-71 (1993).

Petros, P. E. Papa, et al., "Non Stress Non Urge Female Urinary Incontinence—Diagnosis and Cure: A Preliminary Report" Acta Obstet Gynecol Scand, vol. 69 Suppl. 153. pp. 69-70 (1990).

Petros, P. E. Papa, et al., "Part I: Theoretical, Morphological, Radiographical Correlations and Clinical Perspective" Scand J Urol Nephrol, Suppl. 153. pp. 5-28 (1993).

Petros, P. E. Papa, et al., "Part II: The Biomechanics of Vaginal Tissue and Supporting Ligaments With Special Relevance to the Pathogenesis of Female Urinary Incontinence" Scand J Urol Nephrol, Suppl. No. 153, pp. 29-40 (1993).

Petros, P. E. Papa, et al., "Part III: Surgical Principles Deriving From the Theory" Scand J Urol Nephrol, Suppl. No. 153, pp. 41-52 (1993).

Petros, P. E. Papa, et al., "Part IV: Surgical Applications of the Theory—Development of the Intravaginal Sling Plasty (IVS) Procedure" Scand J Urol Nephrol, Suppl. No. 153, pp. 53-54 (1993).

Petros, P. E. Papa, et al., "Pregnancy Effects on the Intravaginal Sling Operation" Acta Obstet Gynecol Scand, vol. 69 Suppl. 153, pp. 77-79 (1990).

Petros, P. E. Papa, et al., "The Autogenic Ligament Procedure: A Technique for Planned Formation of an Artificial Neo-Ligament" Acta Obstet Gynecol Scand, vol. 69 Suppl 153, pp. 43-51 (1990).

Petros, P. E. Papa, et al., "The Combined Intravaginal Sling and Tuck Operation. An Ambulatory Procedure for Cure of Stress and Urge Incontinence" Acta Obstet Gynecol Scand, vol. 69 Suppl 153, pp. 53-59 (1990).

Petros, P. E. Papa, et al., "The Development of the intravaginal Slingplasty Procedure: IVS II—with bilateral 'tucks')", Scand J Urol Nephrol, Suppl. 153. pp. 61-67 (1993).

Petros, P. E. Papa, et al., "The Free Graft Procedure for Cure of the Tethered Vagina Syndrome" Scand J Urol Nephrol, Suppl. No. 153, pp. 85-87 (1993).

Petros, P. E. Papa, et al., "The Further Development of the Intravaginal Slingplasty Procedure: IVS IV—(with "double-breasted" unattached vaginal flap repair and "free" vaginal tapes)" Scand J Urol Nephrol, Suppl. No. 153, pp. 73-79 (1993).

Petros, P. E. Papa, et al., "The Intravaginal Slingplasty Procedure: IVS VI—further development of the 'double-breasted' vaginal flap repair—attached flap" Scand J Urol Nephrol, Suppl. No. 153, pp. 81-84 (1993).

Petros, P. E. Papa, et al., "The Posterior Fornix Syndrome: A Multiple Symptom Complex of Pelvic Pain and Abnormal Urinary Symtoms Deriving From Laxity in the Posterior Fornix of Vagina" Scand J Urol Nephrol, Suppl. No. 153, pp. 89-93 (1993).

Petros, P. E. Papa, et al., "The Role of a Lax Posterior Vaginal Fornix in the Causation of Stress and Urgency Symptoms: A Preliminary Report" Acta Obstet Gynecol Scand, vol. 69 Suppl. 153, 71-73 (1990).

Petros, P. E. Papa, et al., "The Tethered Vagina Syndrome, Post Surgical Incontinence and I-Plasty Operation for Cure" Acta Obstet Gynecol Scand, vol. 69 Suppl. 153, pp. 63-67 (1990).

Petros, P. E. Papa, et al., "The Tuck Procedure: A Simplified Vaginal Repair for Treatment of Female Urinary Incontinence" Acta Obstet Gynecol Scand, vol. 69 Suppl. 153, pp. 41-42 (1990).

Petros, P. E. Papa, et al., "Urethral Pressure Increase on Effort Originates From Within the Urethra, and Continence From Musculovaginal Closure" Neurourology and Urodynamics, vol. 14, pp. 337-350 (1995).

Petros, P. E. Pappa, "Development of Generic Models for Ambulatory Vaginal Surgery—Preliminary Report" International Urogynecology Journal, 9 pages (1998).

Pourdeyhimi, "Porosity of surgical mesh fabrics: New technology", J. Biomed. Mater. Res.: Applied Biomaterials, vol. 23, No. A1, pp. 145-152 (1989), © 1989 John Wiley & Sons, Inc.

Rackley, Raymond R., M.D., et al. "Tension-free Vaginal Tape and Percutaneous Vaginal Tape Sling Procedures" Techniques in Urology, vol. 7, No. 2, pp. 90-100 (2001).

Rackley, Raymond, M.D., "Synthetic slings: Five steps for successful placement" Urology Times, pp. 46, 48-49 (Jun. 2000).

Raz, Shlomo, et al., The Raz Bladder Neck Suspension Results in 206 Patients, The Journal of Urology, pp. 845-850 (Sep. 1992).

Raz, Shlomo, M.D. et at., "Female Urology—Second Edition" University of California at Los Angeles School of Medicine, articles pp. 80-86, 369-381, 382-391, 392-394, 395-398, 435-442, (1996) W.B. Saunders Company.

Raz, Shlomo, M.D., "Modified Bladder Neck Suspension for Female Stress Incontinence" Urology, vol. XVII, No. 1, pp. 82-85 (Jan. 1981) University of California Health Sciences Center, Los Angeles, CA.

Richardson, David A., M.D., et al., "Delayed Reaction to the Dacron Buttress Used in Urethropexy" The Journal of Reproductive Medicine, vol. 29 No. 9, pp. 689-692 (Sep. 1984).

Ridley, John H., M.D., "Appraisal of the Goebell-Frangenheim-Stoeckel sling procedure" Am. J. Obst. & Gynec. vol. 95, No. 5, pp. 714-721 (Jul. 1, 1966).

Roberts, Henry, M.D., M.R.C.O.G., "Cystourethrography in Women" Ethel Bovce University Fellowship vol. 25 No. 293. pp. 253-259 (May 1952) University of Liverpool.

Sloan, W. R., et al., "Stress Incontinence of Urine: A Retrospective Study of the Complications and Late Results of Simple Suprapubic Suburethral Fascial Slings" The Journal of Urology, vol. 110, pp. 533-536 (Nov. 1973).

Spencer, Julia R., et al., "A Comparison of Endoscopic Suspension of the Vesical Neck With Suprapubic Vesicourethropexy for Treatment of Stress Urinary Incontinence" The Journal of Urology, vol. 137, pp. 411-415 (Mar. 1987).

Stamey, Thomas A., M.D., "Endoscopic Suspension of the Vesical Neck for Urinary Incontinence in Females" Ann Surg., vol. 192, No. 4, pp. 465-471 (Oct. 1980).

Stanton, Stuart L., FRCS, PRCOG, "Suprapubic Approaches for Stress Incontinence in Women" JAGS, vol. 38, No. 3, pp. 348-351 (1990), The American Geriatrics Society.

Staskin, David R., et al., "The Gore-tex sling procedure for female sphincteric incontinence: indications, technique, and results" World J Urol., vol. 15, pp. 295-299 (1997) Springer-Verlag.

Studdiford, William E., M.D., "Transplantation of Abdominal Fascia for the Relief of Urinary Stress Incontinence" Am J Obst Gynec, vol. 47, pp. 764-775 (1944) Bellevue Hospital and New York University College of Medicine.

Ulmsten, U., "Female Urinary Incontinence—A Symptom, Not a Urodynamic Disease. Some Theoretical and Practical Aspects on the Diagnosis and Treatment of Female Urinary Incontinence" The International Urogynecology Journal, vol. 6, pp. 2-3 (1995).

Ulmsten, U., et al., "A Multicenter Study of Tension-Free Vaginal Tape (TVT) for Surgical Treatment of Stress Urinary Incontinence" The International Urogynecology Journal, vol. 9, pp. 210-213 (1998).

Ulmsten, U., et al., "A three-year follow up of tension free vaginal tape for surgical treatment of female stress urinary incontinence" The British Journal of Obstetrics and Gynaecology, vol. 106, pp. 345-350 (Apr. 1999).

Ulmsten, U., et al., "An Ambulatory Surgical Procedure Under Local Anesthesia for Treatment of Female Urinary Incontinence" The International Urogynecology Journal, vol. 7, pp. 81-86 (1996).

Ulmsten, U., et al., "Different Biochemical Composition of Connective Tissue in Continent and Stress Incontinent Women" Acta Obstet Gynecol Scand, vol. 66, pp. 455-457 (1987).

Ulmsten, U., et al., "Intravaginal Slingplasty (IVS): An Ambulatory Surgical Procedure for Treatment of Female Urinary Incontinence" Scand J Urol Nephrol, vol. 29, pp. 75-82 (1995) Scandinavian University Press.

Ulmsten, U., et al., "The unstable female urethra" Am. J. Obstet. Gynecol., vol. 144 No. 1, pp. 93-97 (1982).

Walters, Mark D., Percutaneous Suburethral Slings: State of the Art Presented at the conference of the American Urogynecologic Society, Chicago, 29 pages, (Oct. 2001).

Waxman, Steve et al., Advanced Urologic Surgery for Urinary Incontinence, The Female Patient, vol. 21, pp. 93-100 (Mar. 1996).

Webster, George D., "Female Urinary Incontinence" Urologic Surgery—3rd Ed., Ch. 66, pp. 665-679 (1983).

Webster, George D., et al., "Voiding Dysfunction Following Cystourethropexy: Its Evaluation and Management" The Journal of Urology, vol. 144, pp. 670-673 (Sep. 1990) American Urological Association, Inc.

Winter, Chester C., M.D., "Peripubic Urethropexy for Urinary Stress Incontinence in Women" Urology vol. XX, No. 4, pp. 408-411 (Oct. 1982).

Woodside, Jeffrey R., et al., "Suprapubic Endoscopic Veslcal Neck Suspension for the Management of Urinary Incontinence in Myelodysplastic Girls" The Journal of Urology, vol. 135, pp. 97-99 (Jan. 1986).

Zacharin, Robert F., "The suspensory mechanism of the female urethra" Journal of Anatomy, vol. 97, Part 3, pp. 423-427, (1963).

Zacharin, Robert F., FRCS, FRCOG, et al, "Pulsion Enterocele: Long-Term Results of an Abdominoperineal Technique" Obstetrics & Gynecology, vol. 55, No. 2, pp. 141-148 (Feb. 1980) The American College of Ostetricians & Gynecologists.

Zimmem, Phillippe E. et al., "Four-Corner Bladder Neck Suspension" Vaginal Surgery for the Urologist, vol. 2, No. 1, pp. 29-36 (Apr. 1994).

Declaration of Johann J. Neisz with Attachment (Mar. 19, 2004).

Bard, "Uretex Polypropylene Urethral Support—Safety, Simplicity, Flexibility" Marketing Material (2002) 8 pages.

Boston Scientific Corp., Boston Scientific Microvasive, "Precision Tack Transvaginal Anchor System—The Precise Approach to Transvaginal Sling Procedures" Marketing Material (1998) 4 pages.

Boston Scientific Corp., Boston Scientific Microvasive, "Precision Twist Transvaginal Anchor System—Low Profile Design for Precise Anchor Placement" Marketing Material (2000) 2 pages.

Boston Scientific Corp., "Advantage A/T—Surgical Mesh Sling Kit" Marketing Material (2002) 1 page.

Boston Scientific Corp., "Precision SpeedTac—Transvaginal Anchor System" Marketing Material (2002) 1 page.

Ethicon, Inc., TVT Tension-free Vaginal Tape, Gynecare, 23 pages (1999).

Gynecare TVT, "Tension-Free Support for Incontinence" Marketing Material, Gynecare Worldwide (Feb. 2002), 6 pages.

Gynecare, "TVT—Tension-Free Vaginal Tape, Minimally invasive, Highly Effective Treatment for Female Stress Urinary Incontinence" Marketing Brochure, Ethicon, Inc. (1999) 6 pages.

Hernlarnesh USA Inc., "T-Sling (Totally Tension-free) Urinary Incontinence Procedure" Marketing Material (Jan. 2001), 2 pages.

Mentor, "The Strength of Suspend" Marketing Material (Mar. 2000) 6 pages.

Mentor, Sabre, "Generation Now" Marketing Material (May 2002) 4 pages.

Mentor, Sabre, Surgical Procedure, Marketing Material (Aug. 2002) 6 pages.

Mentor-Porges, Trans-obturator tape, Le hamac perinial, Nos references, Marketing Material in French language (2003) 1 page.

Porges U.K. Ltd., "Uratape Perineal Hammock Urethral Support Tape—New Generation of Tape Perineal Implantation" Mentor, Marketing Material (2002) 4 pages.

Safyre, "The Essence of a Contemporary Synthetic Sling—Self-Anchoring Complete Adjustability Elastic" Promedon, Marketing Material (Jan. 30, 2002) 4 pages.

Urogynecology, Product Catalog, eg. SIS Technology, Bladder Suspension, Urodynamics and Urinary Diversion, Incontinence, Cook, Urological Inc. (1996) 36 pages.

Dietz, Hans, MD, et al,, "Does the tension-free vaginal tape stay where you put it?" Am. J. Obstet Gynecol. V. 188, No. 4, pp. 950-953 (2003).

Drutz, H., et al., "Clinical and Urodynamic Re-evaluation of Combined Abdominal Marlex Sling Operations for Recurrent Stress Urinary Incontinence" Int. Urogynecol J. 1: pp. 70-73 (1990).

Flanu, Stefan, et al, Absorbable Polyglactin Mesh for Retropubic Sling Operations in Female Urinary Stress Incontinence, Gyneol. Obstet. Invest. 16, pp. 45-50 (1983).

Mentor-Porges, Come See Us at Booth #28, Marketing Material (Jul. 2002) 1 page.

Mouly, Patrick, et al., "Vaginal Reconstruction of a Complete Vaginal Prolapse: The Trans Obturator Repair" Journal of Urology, Apr. 2003, vol. 169 (4) supplement, p. 183, Abstract # V 702, AUA (Apr. 26-May 1, 2003) Chicago, IL.

Nicita, G. et al. "Six Year Results of Prosthetic Vaginal Surgery for Cystocele Repair" European Urology Supplements 3 (2004) No. 2, p. 50 (Mar. 24-27, 2004).

Ogundipe, Anthony, MD, et al., "Modified Suburethral Sling Procedure for Treatment of Recurrent or Severe Stress Urinary Incontinence" Surg. Gynecol. Obstet., V175, pp. 173-176 (Aug. 1992).

"Safyre and Transobturator", Video file on CD-ROM (2004).

Timmons, M. Chrystie, et al., "Abdominal Sacral Colpopexy in 163 Women with Posthysterectomy Vaginal Vault Prolapse and Enterocele—Evolution of Operative Techniques" J. of Reproductive Medicine, V.35, No. 4, pp. 323-327 (Apr. 1992).

"Vesica Sling Kits with Press-In Percutaneous Anchor System—Simplifying Sling Procedures" Marketing Material, Boston Scientific Corp., Boston Scientific Microvasive, (1998), 4 pages.

Young, Stephen B., et al., "The Mersilene mesh suburethral sling: A clincal and urodynamic evaluation" Am. J. Obstet. Gynecol. V. 173, pp. 1719-1726 (Dec. 1995).

* cited by examiner

METHOD AND APPARATUS FOR TREATING PELVIC ORGAN PROLAPSE

RELATED APPLICATIONS

This application is a divisional of U.S. Ser. No. 11/518,932, filed Sep. 12, 2006 now U.S. Pat. No. 7,811,222, a utility application claiming priority to U.S. Provisional Application 60/716,110, filed Sep. 12, 2005, the entire contents of which is incorporated by reference herein. U.S. patent application Ser. No. 11/518,932 is also a continuation in part of U.S. patent application Ser. No. 10/834,943 filed Apr. 30, 2004 now U.S. Pat. No. 7,500,945, and U.S. patent application Ser. No. 10/840,646 filed May 7, 2004 now U.S. Pat. No. 7,351,197 which are incorporated by reference herein.

BACKGROUND OF THE INVENTION

1. Field of the Invention

The invention relates generally to the treatment of urogenital conditions. More particularly, the invention relates to devices and surgical techniques for use in treating female pelvic organ prolapse.

2. Description of the Related Art

When intra-abdominal pressure pushes the vagina outside the body, vaginal prolapse can develop. In normal circumstances, the levator ani muscles close the pelvic floor, supporting it from below while fascia a ligaments support. Increases in abdominal pressure, failure of the muscles to keep the pelvic floor supported, and damage to the ligaments and fascia all contribute to the development of prolapse. In addition, if a woman has a hysterectomy, the vaginal angle may be altered and ligament support reduced, causing increased pressure at a more acute angle, accelerating the prolapse.

The vagina and uterus are generally composed of two different types of tissue. First, there are fibrous connective tissues that attach these organs to the pelvic walls (cardinal and uterosacral ligaments; pubocervical and rectovaginal fascia). Second, the levator ani muscles close the pelvic floor so the organs can rest on the muscular shelf. It is when damage to the muscles open the pelvic floor or during the trauma of childbirth that the fascia and ligaments are strained. Breaks in the fascia allow the wall of the vagina or cervix to prolapse downward.

A variety of factors can cause genital prolapse in women. It is thought that individual women have differing inherent strength of the relevant connective tissue. The loss of connective tissue strength may be associated with damage at childbirth, deterioration with age, poor collagen repair mechanisms, and poor nutrition. Loss of muscle strength might also be associated with neuromuscular damage during childbirth, neural damage from chronic straining, and metabolic diseases that affect muscle function. Other factors involved in prolapse include increased loads on the supportive system, as seen in prolonged lifting or chronic coughing from chronic pulmonary disease, or some disturbance in the balance of the structural support of the genital organs. Possible factors may also include obesity, constipation, and a history of hysterectomy.

Anterior vaginal wall prolapse causes the vaginal wall to fail to hold the bladder in place. This condition, in which the bladder sags or drops into the vagina, is termed a cystocele. There are two types of cystocele caused by anterior vaginal wall prolapse. Paravaginal defect is caused by weakness in the lateral supports, mainly the attachment of the bladder to the endopelvic fascia; central defect is caused by weakness in the central supports, mainly the fascial layers. A transverse defect, causing cystecele across the vagina, may also occur.

Posterior vaginal wall prolapse results in descent of the rectum into the vagina, often termed a rectocele, or the presence of small intestine in a hernia sac between the rectum and vagina, called an enterocele. There are generally four types of enteroceles based on suspected etiology. Congenital enteroceles are thought to occur because of failure of fusion or reopening of the fused peritoneal leaves down to the perineal body. Posthysterectomy vault prolapses may be "pulsion" types that are caused by pushing with increased intra-abdominal pressure. They may occur because of failure to reapproximate the superior aspects of the cardinal and uterosacral ligaments, pubocervical fascia and the rectovaginal fascia at the time of surgery. Enteroceles that are associated with cystocele and rectocele may be from "traction" or pulling down of the vaginal vault by the prolapsing organs. Finally, iatrogenic prolapses may occur after a surgical procedure that changes the vaginal axis, such as certain surgical procedures for treatment of incontinence. With regard to rectoceles, low rectoceles may result from disruption of connective tissue supports in the distal posterior vaginal wall, perineal membrane, and perineal body. Mid-vaginal and high rectoceles may result from loss of lateral supports or defects in the rectovaginal septum. High rectoceles may result from loss of apical vaginal supports. Posterior or posthysterectomy enteroceles may accompany rectoceles.

Vaginal prolapse and the concomitant anterior cystocele can lead to discomfort, urinary incontinence, and incomplete emptying of the bladder. Posterior vaginal prolapse may additionally cause defecatory problems, such as tenesmus and constipation.

Various techniques have been tried to correct or ameliorate the prolapse and its symptoms, with varying degrees of success. Nonsurgical treatment of prolapse involves measures to improve the factors associated with prolapse, including treating chronic cough, obesity, and constipation. Other nonsurgical treatments may include pelvic muscles exercises or supplementation with estrogen. These therapies may alleviate symptoms and prevent worsening, but the actual hernia will remain. Vaginal pessaries are the primary type of nonsurgical treatment. However there can be complications due to vaginal wall ulceration.

A variety of surgical techniques are used for the treatment of anterior vaginal prolapses. In the small proportion of cases in which the prolapse is caused by a central defect, anterior colporrapphy is an option. This surgery involves a transvaginal approach in which sutures are used to reapproximate the attenuated tissue across the midline of the vagina. More commonly, the prolapse is due to a lateral defect or a combination of lateral and central defects. In these instances, several surgical techniques have been used, such as a combination of an anterior colporrapphy and a site-specific paravaginal repair. Both abdominal and vaginal approaches are utilized. Biological or synthetic grafts have been incorporated to augment repair.

Similarly, the treatment of posterior vaginal prolapses may vary. If symptoms are minimal, nonoperative therapy such as changes in activities, treatment of constipation, and Kegel exercises might be appropriate. Again, both vaginal and abdominal approaches are used, involving sutures to reapproximate the attenuated tissue and possibly a biological or synthetic graft to augment the repair.

The vaginal vault may be attached to the sacrum by use of mesh or fascia in a procedure known as Sacral colpopexy. The surgery may be performed through an abdominal incision or laparoscopically, however certain undesirable complications may occur. If synthetic mesh is used, it is typically carefully customized or assembled into a special shape by the surgeon. Sacral colpopexy can also be a tedious, challenging surgical procedure, with an average procedure length of 247 minutes reported in Winters et al., Abdominal Sacral Colpopexy and Abdominal Enterocele Repair in the Management of Vaginal Vault Prolapse, Urology 56 (Suppl 6A) (2000): 55-63. Some of this time is attributed to the time required for the surgeon to fashion the implant. In addition, it is often required to correct multiple pelvic floor abnormalities simultaneously, which further increases the duration of the surgery.

Another procedure, called sacrospinous fixation, is also used to treat vaginal vault prolapse. This procedure involves attaching the vaginal vault to the sacrospinous ligament, which requires specialized skills and has the disadvantage of tending to place the vagina in an artificial anatomical position.

It is also possible to use various sling procedures to treat prolapse conditions. A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611,515; 5,842,478; 5,860,425; 5,899,909; 6,039,686; 6,042,534; and 6,110,101.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

The TVT Tension-free Vaginal Tape procedure utilizes a Prolene™ nonabsorbable, polypropylene mesh to treat incontinence. A plastic sheath surrounds the mesh and is used to insert the mesh into the patient. Abdominal and vaginal incisions are made, followed by implantation of the mesh using two curved, needle-like elements to push the mesh through the vaginal incision and into the paraurethral space. Using the procedure described elsewhere, the mesh is looped beneath the bladder neck or urethra. The sling is positioned to provide appropriate support to the bladder neck or urethra. When the TVT mesh is properly positioned, the cross section of the mesh should be substantially flat. In this condition, the edges of the mesh do not significantly damage tissue. Shortcomings and attempts to address these shortcomings and other problems associated with certain tape procedures are disclosed in PCT publication nos. PCT WO 00/74613 and PCT WO 00/74594.

Due to the tough fibrous nature of fascia and muscle tissues, forceps or similar instruments are needed to withdraw the needles through the abdominal wall. However, the smooth surface of the needles, which facilitates insertion through the tissues, prevents secure attachment of the forceps onto the needles, causing slippage or detachment of the forceps during the withdrawal procedure. Improper placement of certain meshes is also particularly troublesome. If the mesh is too loosely associated with its intended physiological environment, the mesh may be ineffective in supporting the urethra and treating incontinence. Surgeons may exacerbate certain problems by improperly attempting to adjust the tension of a sling. If insufficient adjustment force is applied, the sling will simply exhibit a memory property and return to its original, unacceptable position. As a result, surgeons are tempted to use a great deal of force in order to loosen a sling that is perceived to be too tightly associated with its intended physiological environment. If excessive force is applied, the mesh will plastically deform and the cross section of the mesh will become arcuate. Excessive deformation may also result in a lack of efficacy.

U.S. Pat. No. 6,695,855 (Gatson) describes a device for treating a prolapse by vaginal suspension. The device includes an elongated, flexible pierced material, a suture connected to the material, and a suture needle joined to the suture. The device is long enough to enable posterior suspension of the vagina at the front part of the sacrum. The other end of the device includes a distal portion having a width such that it can cover at least a large part of the posterior part of the vagina, a rounded cut-out with dimensions that enable it to be engaged around the base of the vagina on at least a large part of the lower half of the wall of the vagina. The suture is connected to the article so that it is offset sidewise in relation to the cut-out.

PCT Publication No. WO 00/27304 (Ory) discloses a suspension device for treating prolapse and urinary incontinence. The device comprises at least one filiform suspension cord with limited elasticity and at least two anchoring parts linked to the ends of the cord.

U.S. Pat. No. 5,112,344 and PCT Publication No. PCT/US02/32284 disclose surgical devices for female pelvic health procedures. The IVS Tunneller device (available from U.S. Surgical, Norwalk, Conn.) comprises a fixed delta wing handle, a hollow metal tube, and a stylet that is placeable within the tube. The stylet has a rounded plastic tip on one end and an eyelet on the other end. The device may be used to implant a polypropylene tape for infracoccygeal sacropexy and other surgical procedures. A single rigid, hollow, metal tube is associated with the IVS Tunneller device. This tube passes through two separate regions of the patient's body with the attendant risk of cross-contamination. The outer diameter is also relatively large (about 0.25 inches) with the attendant risk of tissue damage due to such large diameter. The polypropylene tape supplied with the IVS Tunneller is of a thin, rectangular shape and is not believed to be optimally sized and shaped to afford concomitant procedures such as enterocele, cystocele, and/or rectocele repairs.

There is a need for a minimally invasive yet highly effective device and method that can be used to treat pelvic organ prolapse with minimal or no side effects. Such a device should reduce the complexity of procedures that are currently available while being biocompatible, adjustable, and non-toxic. Treatment methods using the device should reduce pain, operative risks, infections and post operative hospital stays, and generally improve a patient's quality of life.

SUMMARY OF THE INVENTION

The present invention is directed to an apparatus for treating pelvic organ prolapse in a patients. The apparatus includes a central support portion having multiple configurations of ends. A first elongated end portion is connected to said first end of said support portion. The first elongated end portion includes a first dilator configured to attach securely with a tip of a needle. A second elongated end portion is connected to said second end of said support portion. The second elongated end portion includes a second dilator configured to attach securely with a tip of a needle. The first and second needles include a straight portion, a tip, a first radius, and a second radius distinct from the first radius. The first radius and the second radius are disposed between the straight portion and the tip.

The method of treatment is one that allows the operator to know the location of the instruments, as final passage of the needle is aided by the operator's use of his finger, making the method less risky for the patient. The apparatus and method is convenient for the operator, in that the apparatus is relatively simple to operate and contained within the described kit. The sling portion is relatively extensible compared to the prior art. The needle is of a small diameter which reduces the risk of trauma.

The method for repairing pelvic organ prolapse in a patient generally includes the steps of using a first needle to establish a first pathway in tissue on a first side of said prolapsed organ. The pathway extends between an external perirectal region to a region of an ischial spine of the patient. The first needle comprises a tip, a straight portion, a first radius, and a second radius distinct from the first radius. The first radius and the second radius are located between the straight portion and the tip. The method also includes the step of using a second needle to establish a second pathway in tissue on a contralateral side of said prolapsed organ. The pathway extends between an external perirectal region to a region of an ischial spine of the patient. The second needle comprises a tip, a straight portion, a first radius, and a second radius distinct from the first radius. The first radius and the second radius are located between the straight portion and the tip. The method also includes the step of positioning a support member in a position to reposition a prolapsed organ in a organ's anatomically correct location. The support member comprises a support portion having a first and second end, first end portion, and second end portion. The first end portion and second end portion are respectively attached to the first end and the second end. Next, the method includes connecting the end portions to the tips of the respective needles and introducing the first end portion through the first pathway by removing the first needle from the first pathway, and introducing said second end portion through said second pathway by removing the second needle from the second pathway. Lastly, the method includes the step of adjusting the first end portion and the second end portion so that the support member is in a therapeutic relationship to a tissue of the prolapsed organ that is to be supported.

In another embodiment, the invention includes a kit for repairing pelvic organ prolapse in a patient. The kit includes a support member comprising a support portion and two end portions. At least one of the end portions further comprises a removable plastic sheath. A first needle includes a first handle, a first tip, a first radius, and a second radius, wherein the first needle is configured to atraumatically form a first pathway through tissue adjacent to said prolapsed organ. The pathway extends between an external perirectal region and a region of an ischial spine of the patient. A second needle includes a second handle, a second tip, a first radius, and a second radius. The second needle is configured to atraumatically form a second pathway through tissue adjacent to the prolapsed organ.

In yet another embodiment, the invention includes the steps of establishing a first pathway between the external perirectal region of the patient and the region of the ischial spine space in tissue on one side of the prolapsed organ, and establishing a second pathway in tissue on the contralateral side of the prolapsed organ. A support member including a central support portion and two end portions is positioned beneath the prolapsed organ in such a way as to allow repositioning of the organ into its anatomically appropriate location. The end portions of the support member are introduced through the respective tissue pathways. The end potions are adjusted so that the support member is located in a therapeutic relationship to the prolapsed organ that is to be supported.

An alternative embodiment of the invention includes a method directed to treatment of posterior vaginal prolapse. In other embodiments, the method is directed to treatment of vaginal vault prolapse, enterocele, rectocele, or a combination of more than one of these conditions. In another embodiment, the step of establishing the two tissue pathways between the external perirectal region and the region of the ischial spine of the patient, includes the steps of making a midline incision across the vagina to create access to the region of the ischial spine, through sharp and blunt dissection, and making an incision lateral and posterior to the rectum in the skin of a buttocks. A needle is passed from the incision lateral and posterior to the rectum toward the vaginal incision. The tip of the needle is palpated distal and inferior to the ischial spine and then passed through the coccygeous muscle. This step is performed on a first side, then on the contralateral side.

Further, in another embodiment, the step of positioning a support member in a position to support the prolapsed organ in its anatomically correct position includes the step of connecting the support member to the tip of the passed needle, as disclosed in U.S. Pat. No. 6,652,450, which is incorporated by reference. The step of introducing the end portions through the tissue pathways includes the step of retracting back through the respective pathways a needle to which the end portions have been connected. The step of adjusting the end portions so that the support member is in a therapeutic relationship to the prolapsed vagina that is to be supported further includes the steps of attaching the support member to the vaginal wall with sutures, ensuring the vaginal vault is in an appropriate anatomical position, removing the sheath, and adjusting the support member by manipulation of the end portions.

The present invention further provides an apparatus for treatment of pelvic organ prolapse. The apparatus broadly includes a support portion with two ends, for placement in a therapeutically effective position, and two elongated end portions connected respectively to each end of the support portion.

In one embodiment of the invention, the apparatus includes repositioning means for effecting tightening or loosening of the apparatus without adversely affecting its therapeutic efficacy. According to an embodiment, the repositioning means includes at least one filament threaded along at least one end portion. The repositioning means may include at least one removable plastic sheath on at least one end portion, wherein the sheath is configured to affect tightening of the apparatus when the apparatus is partially implanted and the sheath is removed.

In one embodiment, the support portion of the apparatus is substantially rectangular, with two long sides and two short sides. The end portions are connected to the first and second long sides, respectively.

In another embodiment, the apparatus is substantially one tape, in which the support portion is a wider center section, relative to the two end portions, in which the support and the end portions are substantially one tape. Such an embodiment would allow for easier and more secure suture attachment.

In another embodiment, the support portion is of a different material in order to provide for better suture retention.

In another embodiment, the support portion of the apparatus includes first and second elongated portions and means for inserting and securing a biological graft material between the first and second elongated portions.

In another embodiment, the support portion of the apparatus is made from a polypropylene monofilament mesh. At least one of the end portions is made from a polypropylene monofilament mesh according to one embodiment.

In one embodiment, at least one of the end portions of the support member includes a connector configured to attach securely with the end of the needle.

Another aspect of the present invention is a mesh implant that is self-fixating, without the need to pass through an extensive amount of tissue. In a preferred embodiment, lateral and central support for the prolapsed organ (such as a cystocele) is provided with one structure. The implant of this embodiment includes a middle section structured to provide support for the prolapsed organ (such as the anterior vaginal wall in a cystocele), with one or more pairs of legs extending from left and right aspects of the middle section. The implant may be made from a single material or from a combination of materials. The implant can be fixed via a tissue anchor on one or more of the legs. In this embodiment, the legs are pushed up to the arcus where they are fixed.

Prolapsed organs, including cystocele, are graded based on their severity. For example, a grade 1 cystocele is mild, with the bladder drooping only a short way into the vagina. More severe cystocele are graded up to a grade 4 custocele. In the mesh support having one or more pairs of legs, the number of legs varies based on the severity of the prolapse. For example, a grade 2-3 prolapse may require one or two pairs of legs to provide adequate support, while a grade 3 or 4 prolapse may require three or more pairs of legs. In addition, posterior legs are provided to allow the surgeon to attach the vault in the case of a total anterior repair. These arms associated with the vault can be attached to the uterosacral ligaments.

The self-fixating mesh implant may be placed using needles and dilators, as discussed herein for other embodiments of the present invention. The dilator may be designed in such a fashiob to remain in the body and serve as a tissue anchor until sufficient tissue has ingrown into the mesh. The dilator may also be bioresorbable. The legs of the implant are extended outward from the middle portion to the arcus tendineus of the patient, to which the legs are fixed. Some legs are implanted via a transobturator approach, such as the approach described in U.S. Pat. No. 7,070,556, the contents of which are herein incorporated by reference. Likewise, the legs may be implanted via a transvaginal, as described herein, going to the arcus or the obturator foramen, but not out of the body through a skin incision. The present invention also provides a needle for the placement of such a self-fixating implant. The needle adapts to the dilator to allow it to be pushed into place and released. The needle may include markers to indicate the penetration depth and corresponding anatomical placement areas corresponding to the number of legs in the mesh.

The present invention also provides a kit including the elements for practice of the present method. The kit broadly includes a means for repositioning and supporting the prolapsed organ in a physiologically correct position and a means for attaching said repositioning and supporting means to an appropriate anatomical structure.

In yet another embodiment, the kit of the present invention includes a support member including a support portion and two end portions, wherein at least one end portion includes a support portion and two end portions, wherein at least one end portion includes a removable plastic sheath, first and second needles configured to atraumatically form first and second pathways through tissue adjacent to the prolapsed organ, respectively, and handles for directing the needles.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
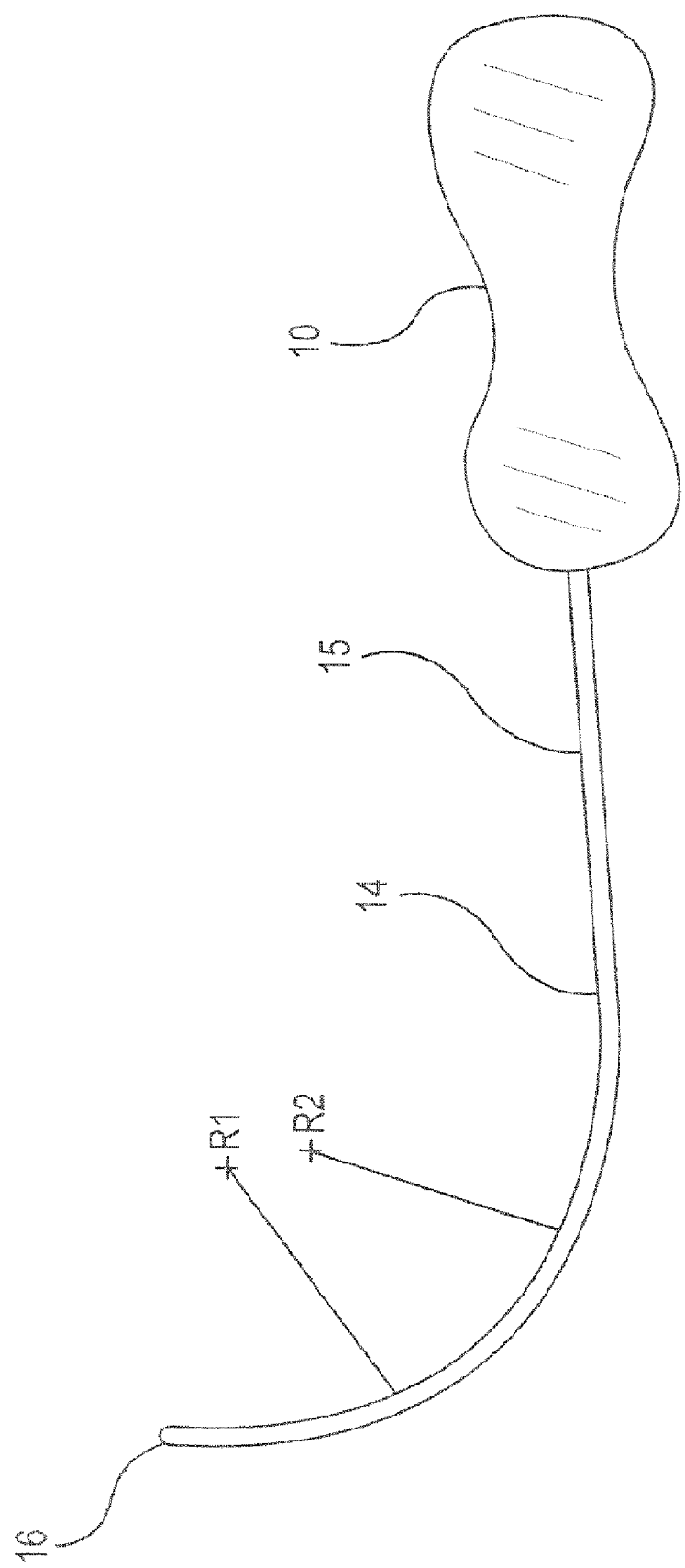
FIG. 1 is a side perspective view of a multi radii needle.

Referring now to the drawings, wherein like reference numerals designate identical or corresponding parts throughout the several views, FIG. 1 shows a needle 14 and handle 10 suitable for use in the present invention. Needle 14 terminates in a tip 16. Needle 14 comprises a generally straight section 15 near handle 10. In one embodiment, the straight section 15 shown in FIG. 1 is between about 4 inches and about 8 inches, preferably between about 5 inches and about 7 inches, more preferably between about 5.5 inches and about 6.5 inches.

The portion of needle 14 between straight section 15 and tip 16 includes a multi radii bend defined by a first radius R1 and a second radius R2, distinct from the first radius. The first radius R1 is generally between about 2 inches and about 4 inches, preferably between about 2.5 inches and about 3.5 inches. The second radius R2 is generally larger than R1. In one embodiment, R2 is between about 4 inches and about 6 inches, preferably between about 4.5 inches and 5.5 inches. This multi-radii bend allows for at least 1 cm of additional curvature of tip 16 for easier final passage past the ischial spine of a patient. It also enables an easier connection between the tip 16 and a mesh support structure. Moreover, the multi-radii bend provides a physician with better control of the tip 16 during a procedure.

Figure 2:
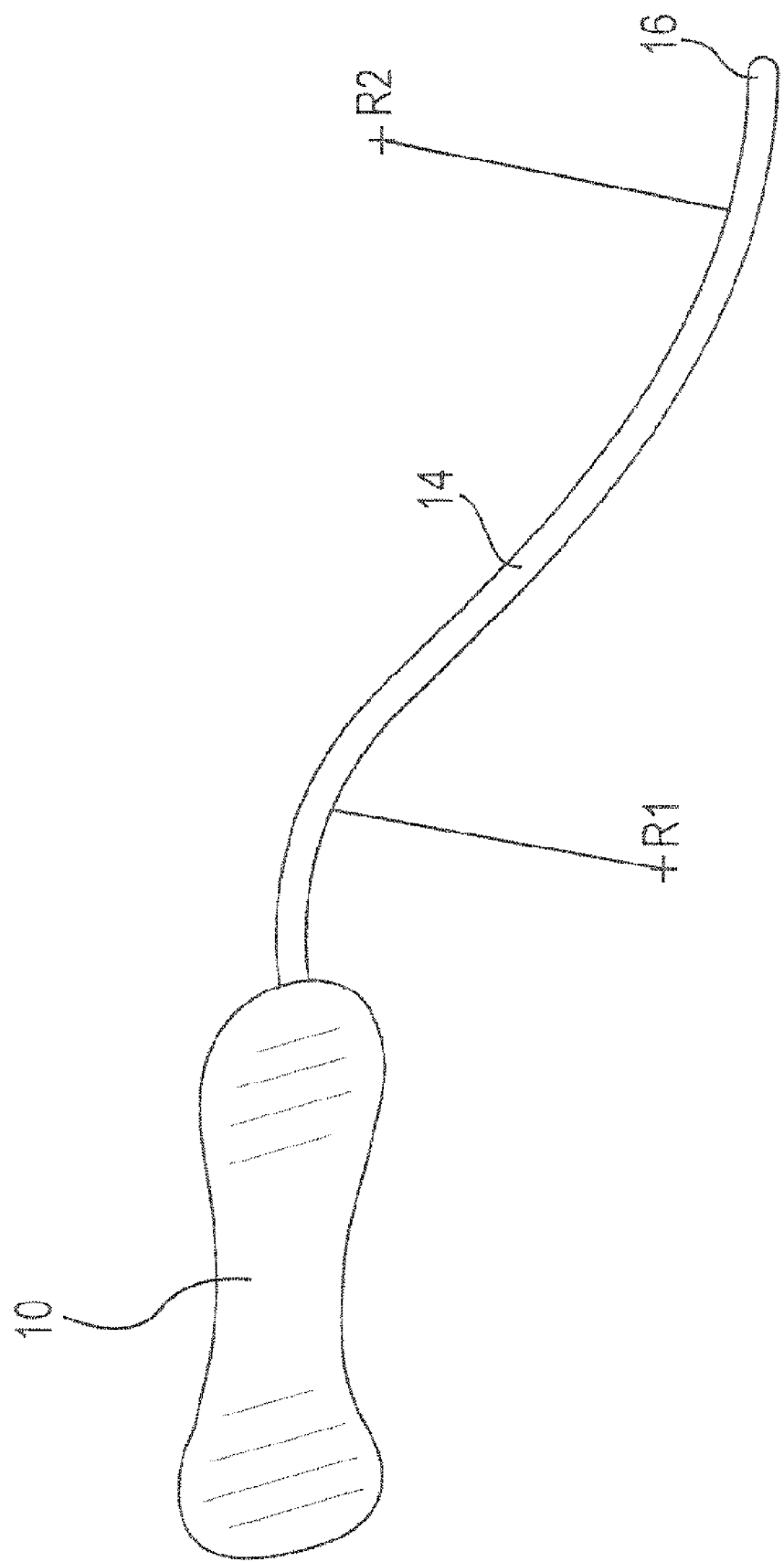
FIG. 2 is a side perspective view of an alternative embodiment of a multi radii needle.

FIG. 2 shows a needle 14 with an alternative multi-radii configuration. In this configuration first radius R1 is on the opposite side of the needle 14 from the second radius R2. As shown in FIG. 2, first radius R1 is smaller than the second radius R2. The tip 16 of needle 14 generally lines in a line parallel to the line disposed within handle 10.

Figure 3:
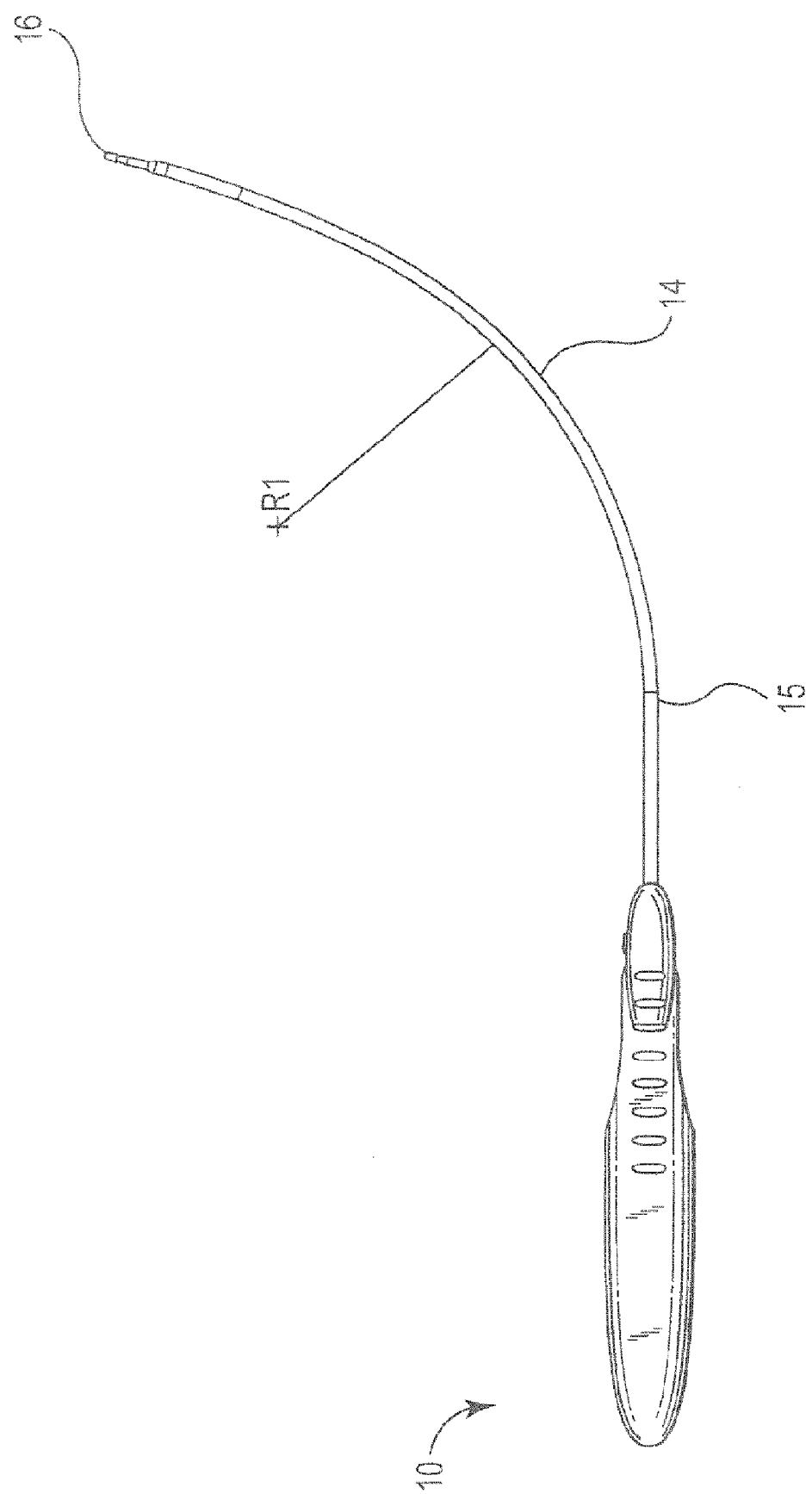
FIG. 3 is a side perspective view of another alternative embodiment of a needle.

FIG. 3 shows a needle 14 with a single-radii configuration. In this configuration, needle 14 forms a single radius R1 which terminates at tip 16. Straight section 15 is disposed between handle 10 and the portion where radius R1 begins. The tip 16 of needle 14 lines in a line generally skewed from the line disposed within handle 10.

Figure 4:
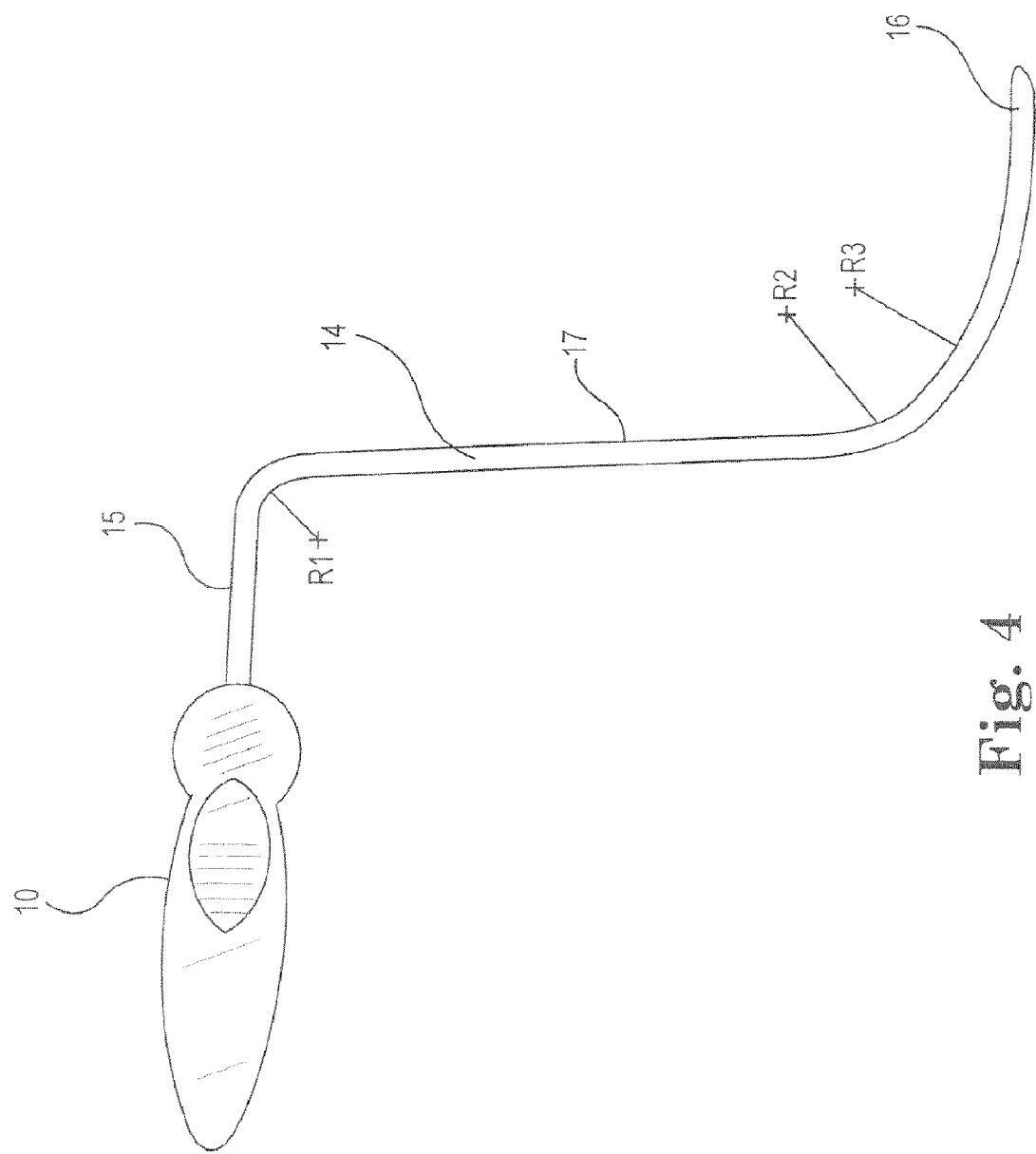
FIG. 4 is a side perspective view of yet another alternative embodiment of a multi radii needle.

FIG. 4 shows an alternative embodiment of a needle 14 which includes three radii R1, R2, and R3. In this embodiment, needle 14 is attached to handle 10 and terminates in tip 16. A first radius is disposed between straight section 15 and straight section 17. Straight section 15 is disposed between handle 10 and first radius R1. Second radius R2 and third radius R3 is disposed between straight section 17 and tip 16. First radius R1 is on the opposite side of the needle from second radius R2 and third radius R3. Moreover first radius is smaller than second radius R2 and third radius R3. This enables straight section 15 to be approximately perpendicular to straight section 17. The tip 16 of needle 14 lies in a line generally parallel to the line disposed in handle 10.

Figure 5:
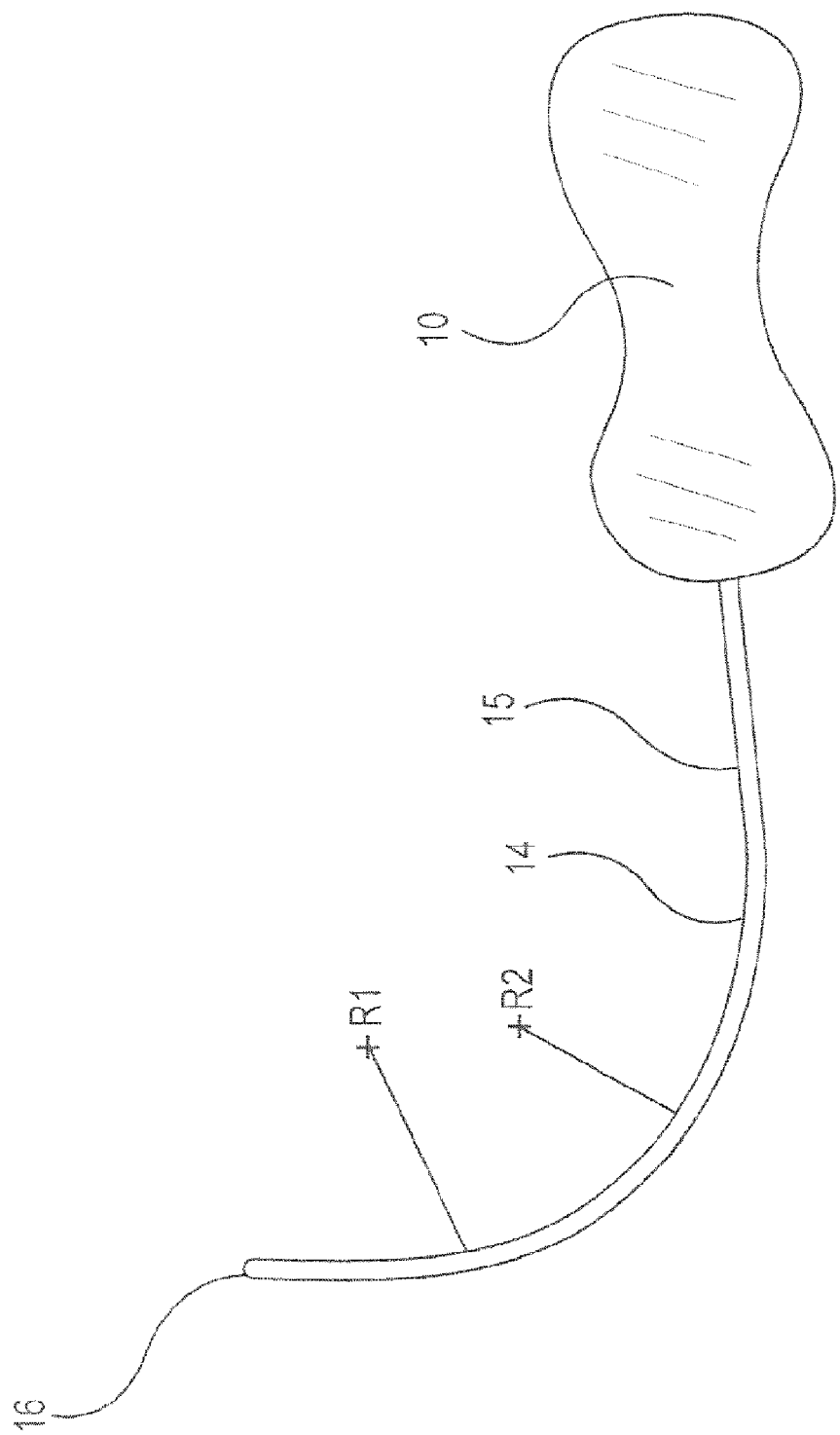
FIG. 5 is a side perspective view of a multi radii needle with short needle shank.

FIG. 5 shows an alternative embodiment of the needle shown in FIG. 1. FIG. 5 shows a needle 14 which terminates in a tip 16. Needle 14 comprises a generally straight section 15 near handle 10. The straight section 15 of the needle in FIG. 5 is at least 2 cm shorter than the straight section of the needle shown in FIG. 1. In one embodiment, the straight section 15 shown in FIG. 5 is between about 3 inches and about 7 inches, preferably between about 4 inches and about 6 inches, more preferably between about 4.5 inches and about 5.5 inches.

With continued reference to FIG. 5, the portion of needle 14 between straight section 15 and tip 16 includes a multi radii bend defined by a first radius R1 and a second radius R2, distinct from the first radius. The first radius R1 is generally between about 2 inches and about 4 inches, preferably between about 2.5 inches and about 3.5 inches. The second radius R2 is generally larger than R1. In one embodiment, R2 is between about 4 inches and about 6 inches, preferably between about 4.5 inches and 5.5 inches. This multi-radii bend allows for at least 1 cm of additional curvature of tip 16 for easier final passage past the ischial spine of a patient. It also enables an easier connection between the tip 16 and a mesh support structure. Moreover, the multi-radii bend, coupled with the shortened straight section 15, provides a physician with increased control of the tip 16 during a procedure. Furthermore, the shortened straight section 15 more easily prevents flexure of the needle 14 by providing increased rigidity.

A variety of needle designs and/or configurations disclosed herein may be used. However, all references hereinafter will be made to the dual radii needles of FIG. 1 and FIG. 5 in the spirit of brevity and reader convenience.

Overall, the shape of the needle 14 should facilitate and provide controlled passage of the needle 14 through tissue as required. The ends or tip of the needle 14 are generally not sharpened, but may be tapered to afford easy passage through tissue while providing a blunt surface that avoids cutting sensitive tissue such as the bowel. It is preferred that the diameter of the needle 14 be slightly larger relative to the prior art to reduce tissue trauma and make palpation easier. In one embodiment, the diameter of needle 14 is between about 0.100 inches and about 0.150 inches, preferably between about 0.120 inches and about 0.130 inches, more preferably about 0.125 inches.

The needle 14 is made of a malleable, yet durable, biocompatible surgical instrument material such as, but not limited to, stainless steel, titanium, Nitinol, polymers, plastics and other materials, including combinations of materials. The needle 14 should have sufficient structural integrity to withstand the various forces (e.g., forces caused by dilator attachment, cystoscopy aid passage, and penetration/passage of the needle 14 through the various tissues) without undergoing any significant structural deformation.

FIGS. 1-5 show needle tip 16. Needle tip 16 is optionally adapted to connect securely to a connector on the end of a sheath associated with as least one of the end portions of a support member. Many different configurations of such a system are known in the art and within the scope of the present invention. Several configurations are disclosed in U.S. Pat. No. 6,652,450, which is incorporated herein by reference.

Figure 6:
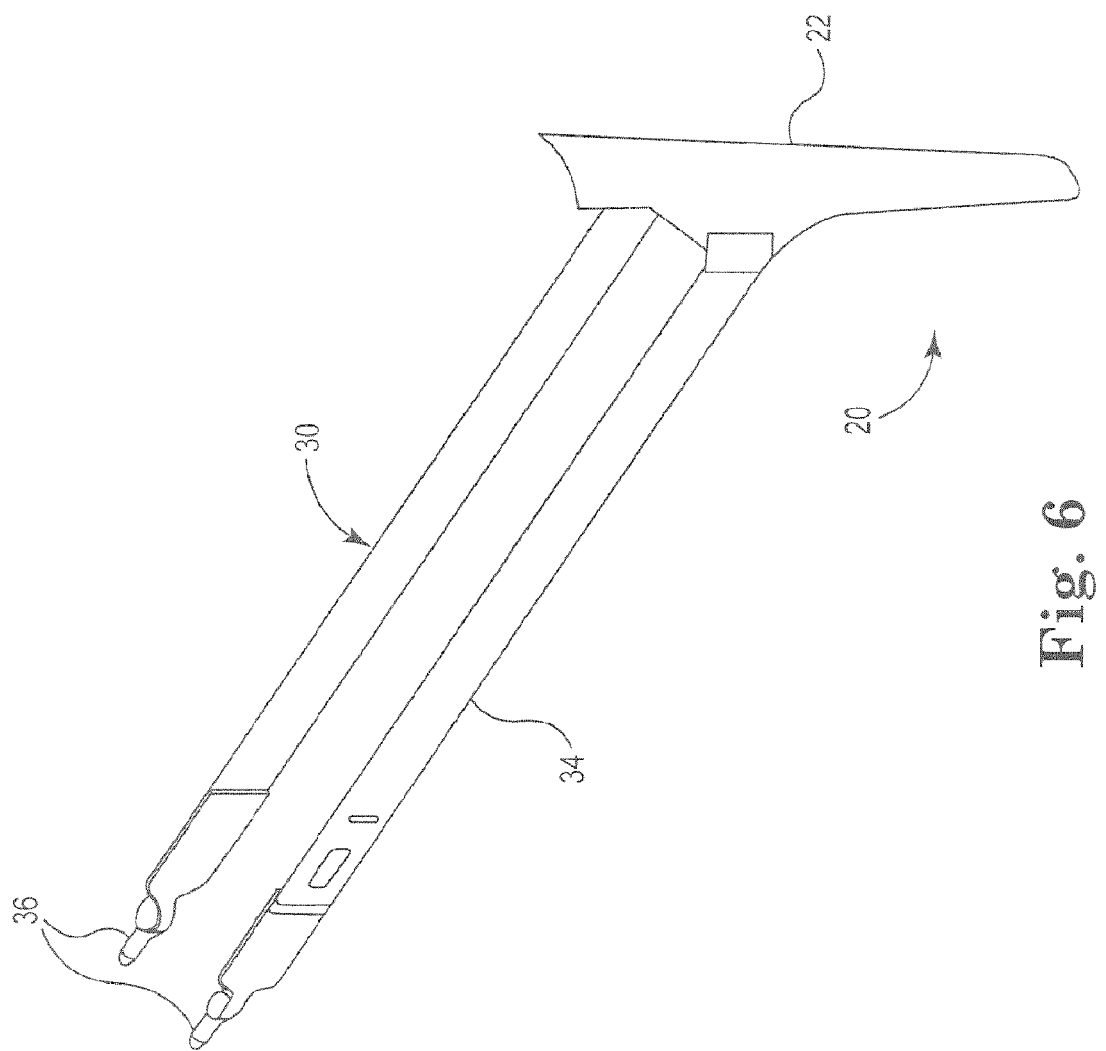
FIG. 6 is a perspective view of the support member combined with a sheath and a dilator.

Following passage through the pathways, the needle tip is connected to a support member of the present invention. Following proper positioning of the support member, the needles are retracted back through the skin incision, carrying the end portions of the support member to the skin incision. FIG. 6 shows an embodiment of the support member 20 of the present invention. The support member 20 is a mesh fabric including the support portion 22 and two end portions 30 and 34. In various embodiments of the invention, the support member may be a one piece mesh with the support portion substantially continuous with the end portions.

Many different types of mesh are known in the art and may be suitable for the present invention. Both biocompatible absorbable and non-absorbable yarns can be used to make the surgical meshes required. Suitable non-absorbable materials for use in the present invention include, but are not limited to, cotton, linen, silk, polyamides (e.g. polyhexamethylene adipamide (nylon 66), polyhexamethylene sebacamide (nylon 610), polycapramide (nylon 6), polydodecanamide (nylon 12) and polyhexamethylene isophthalamide (nylon 61) copolymers and blends thereof), polyesters (e.g. polyethylene terephthalate, polybutyl terephthalate, copolymers and blends thereof), fluoropolymers (e.g. polytetrafluoroethylene and polyvinylidene fluoride) polyolefins (e.g. polypropylene including isotactic and syndiotactic polypropylene and blends thereof, as well as, blends composed predominately of isotactic or syndiotactic polypropylene blended with heterotactic polypropylene (such as are described in U.S. Pat. No. 4,557,264 issued Dec. 10, 1985 assigned to Ethicon, Inc. hereby incorporated by reference) and polyethylene (such as is described in U.S. Pat. No. 4,557,264 issued Dec. 10, 1985 assigned to Ethicon, Inc. hereby incorporated by reference)) and combinations thereof.

Suitable absorbable materials for use as yarns include but are not limited to aliphatic polyesters which include but are not limited to homopolymers and copolymers of lactide (which includes lactic acid and meso lactide), glycolide (including glycolic acid), epsilon.-caprolactone, p-dioxanone(1, 4-dioxan-2-one), trimethylene carbonate(1,3-dioxan-2-one), alkyl derivatives of trimethylene carbonate, delta-valerolactone, beta-butyrolactone, gamma-butyrolactone, epsilon-decalactone, hydroxybutyrate, hydroxyvalerate, 1,4-dioxepan-2-one (including its dimmer 1,5,8,12-tetraoxacyclotetradecane-7,14-dionc), 1,5-dioxepan-2-one, 6,6-dimethyl-1,4-dioxan-2-one and polymer blends thereof.

In the present invention, the mesh is preferably fabricated from a 4.0 mil diameter monofilament polypropylene yarn by employing methods known in the art and described in "Warp.

Knitting Production" by Dr. S. Raz, Melliand Textilberichte GmbH, Rohrbacher Str. 76, D-6900 Heidelberg, Germany (1987), the contents of which are incorporated by reference herein. U.S. Pat. No. 6,638,284 is also herein incorporated by reference in its entirety.

A preferred mesh for use in the present invention is a polypropylene mesh possessing a thickness of about 0.021 inches, has about 27.5 courses per inch, and 13 wales per inch. It has three bar warp knit construction with a bar pattern set-up of #1: 1/0, 2/3, 2/1, 2/3, 1/0, 1/2, 1/0, 1/2: #2: 1/0, 2/3, 2/3, 1/0: #3: 2/3, 1/0, 1/2, 1/0, 2/3, 2/1, 2/3, 2/1.

In an alternative embodiment, the apparatus of the present invention can have different mesh knits in the support member and the end portions. Such a construction would allow use of the optimum knit for support or anchoring. Such an apparatus could be manufactured by use of variable knitting and/or variable heat-setting techniques.

Figure 7:
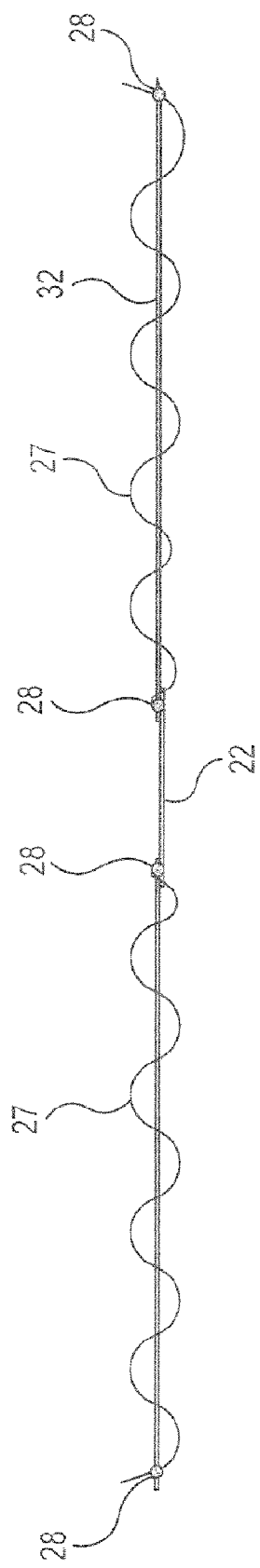
FIG. 7 is a side view of the support member showing a filament tension control member.
Figure 8:
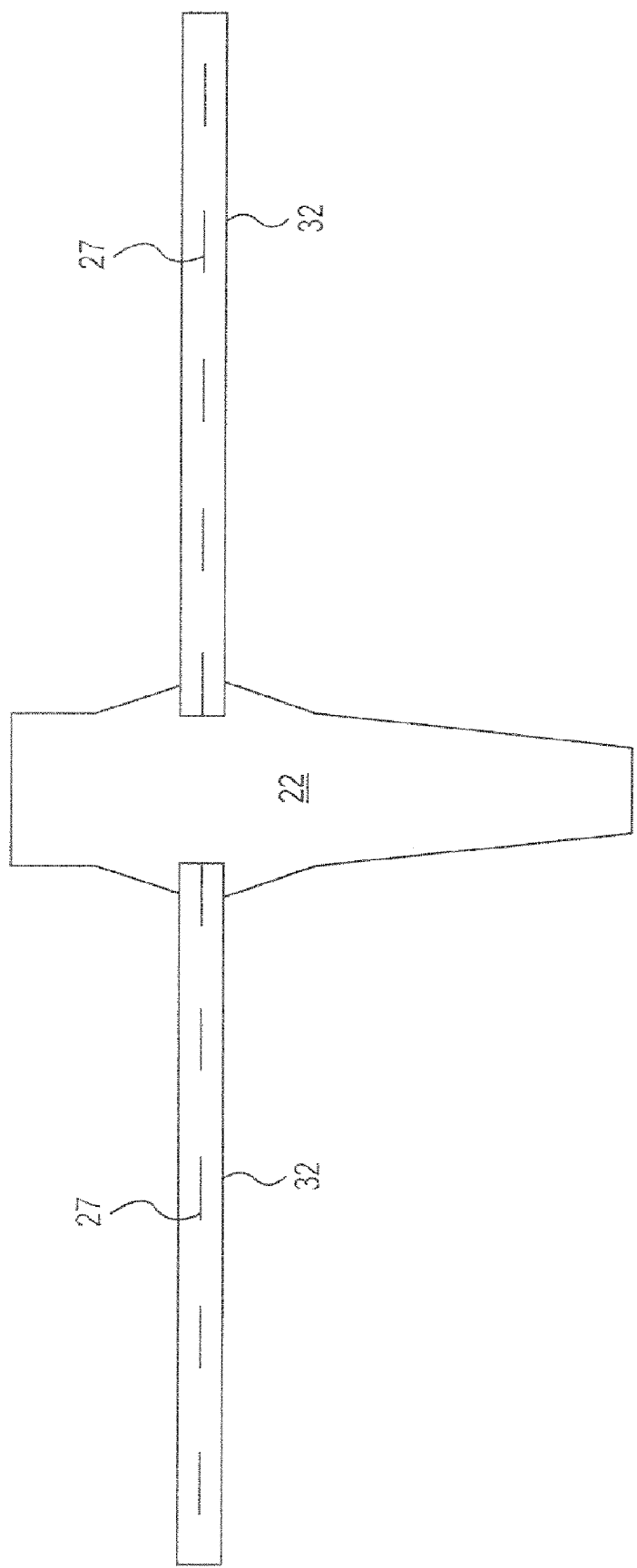
FIG. 8 is a top view of an embodiment of the support member showing a filament tension control member.

FIGS. 7 and 8 illustrate the tension control member 27. The tension control member 27 serves as a repositioning means to effect tightening or loosening of the apparatus without adversely affecting the therapeutic efficacy of the apparatus.

Several different embodiments of tension control member 27 are within the scope of the present invention. In the illustrated embodiment, tension control member 27 is a monofilament fiber woven into the support member and attached to the support member via attachment points 28 located near the support portion 22 of the support member.

Other attachment configurations for the tension control member are also included within the scope of the claimed invention. Several variations of the tension control member are described in U.S. Pat. No. 6,652,450, which is incorporated by reference in its entirety.

The tension control member enables surgeons to easily increase (tighten) or decrease (loosen) the support member tension during the surgical procedure. To reduce the tension of the support member using the tension control member 27, the surgeon contacts the support member and tension control member 27 adjacent the prolapsed organ and pulls away from the organ. The tension of the central portion may be increased by grasping the support member and tension control member 27 above the vaginal incision and pulling upward. One or both end portions of the support member, and tension control member may be grasped to increase the tension of the support member, effecting tightening by pulling the end portions out at the incisions in the buttocks. Affording adjustment of the support member facilitates proper support member placement and helps avoid complications such as recurrence and tissue erosion arising out of improper placement.

The individual fibers or filaments comprising the tension control member may be extruded, woven, braided, spun, knitted, non-woven or have other similar configurations. Tension control member properties, such as tensile strength, elongation at break point, stiffness, surface finish, etc., may be similar to or different from those of the support member and may vary along the length of the support member.

Figure 9:
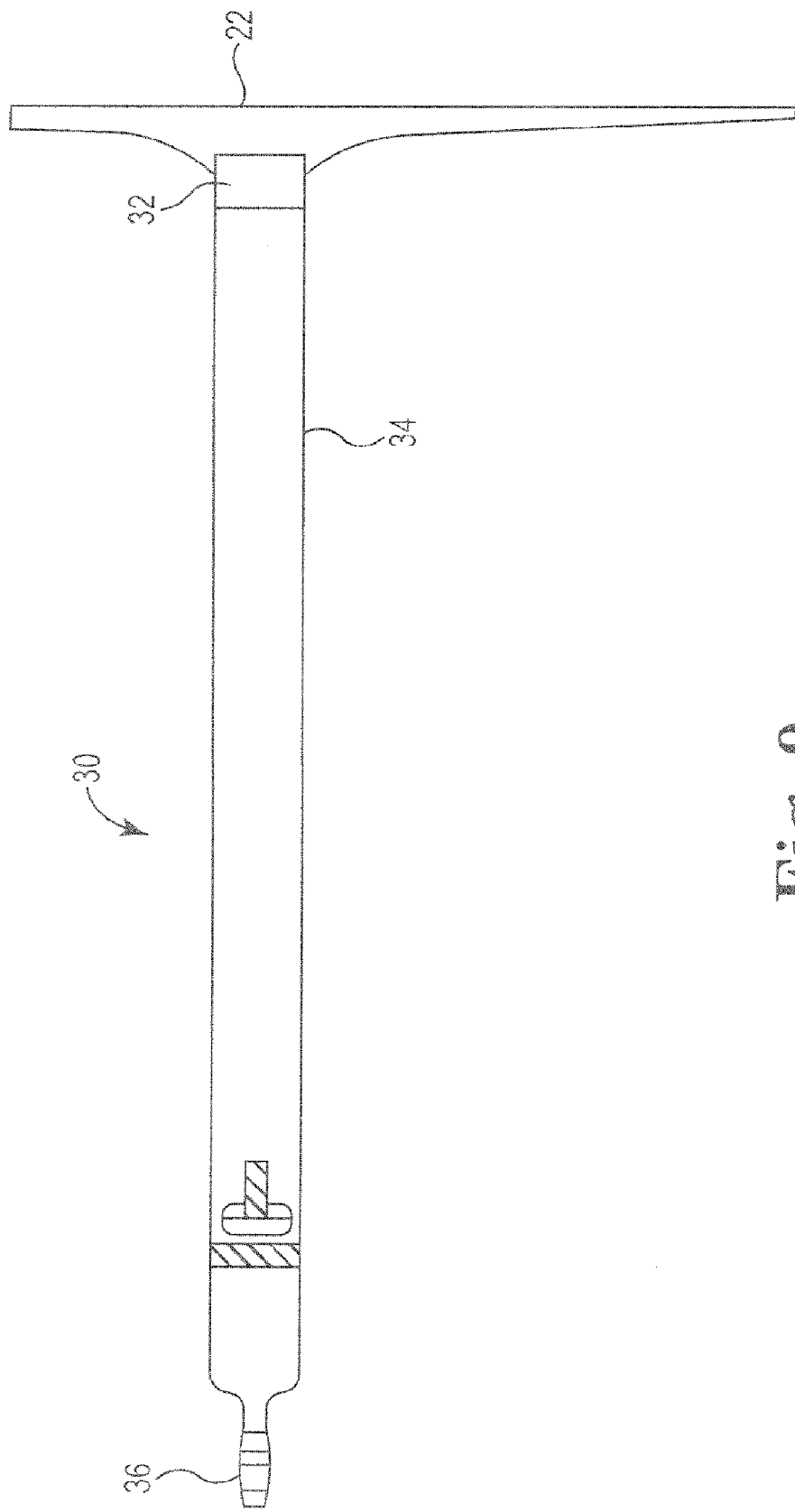
FIG. 9 is a side perspective view of the support member combined with a sheath and a dilator.

FIGS. 6 and 9 show a mesh/sheath assembly. In this preferred embodiment, the end portions 32 of the support member are substantially enclosed by a sheath 34. The sheath acts to ease the passage of the mesh end portions 32 through the tissue and to protect the mesh from deformation. The sheath 34 further serves to maintain the mesh in a more sterile condition because, prior to removal of the sheath, the mesh itself has not contacted the vagina. The sheath 34 further provides a means of adjusting the positioning of the support member through manual manipulation of the sheath 34 before their removal. The sheath 34 may optionally further comprise a connecting mechanism to affect a secure attachment to the end of the needle. Such mechanism may be one of many different configurations known in the art, such as those keying configurations disclosed in U.S. Pat. No. 6,652,450, which is incorporated by reference. A preferred embodiment comprises a loop for attachment of the end portions to the needle. This loop is enlarged to allow a surgeon to place his finger through the loop and push the connector onto the needle.

Figure 10:
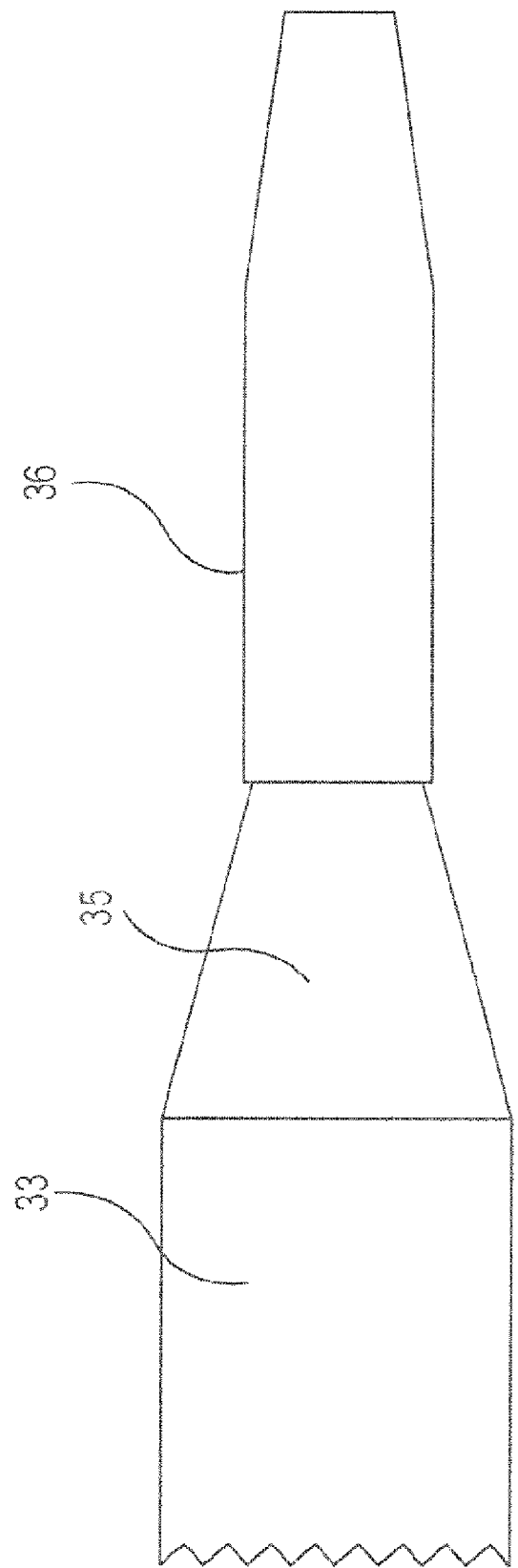
FIG. 10 is a side view of a dilator with low-profile riveted connection.

FIG. 10 shows the attachment of the dilator 36 to the end portion 33 of the support member. A transition zone 35 is disposed between end portion 33 and dilator 36. Transition zone 35 is comprised of a riveted synthetic cape which provides a tapered transition from end portion 33 to dilator 36. In a preferred embodiment, transition zone 35 is at least partially disposed inside dilator 36. This configuration helps minimize snagging of pelvic tissue on the transition zone 35 and end portion 33 as the dilator 36 is pulled through tissue.

Figure 11:
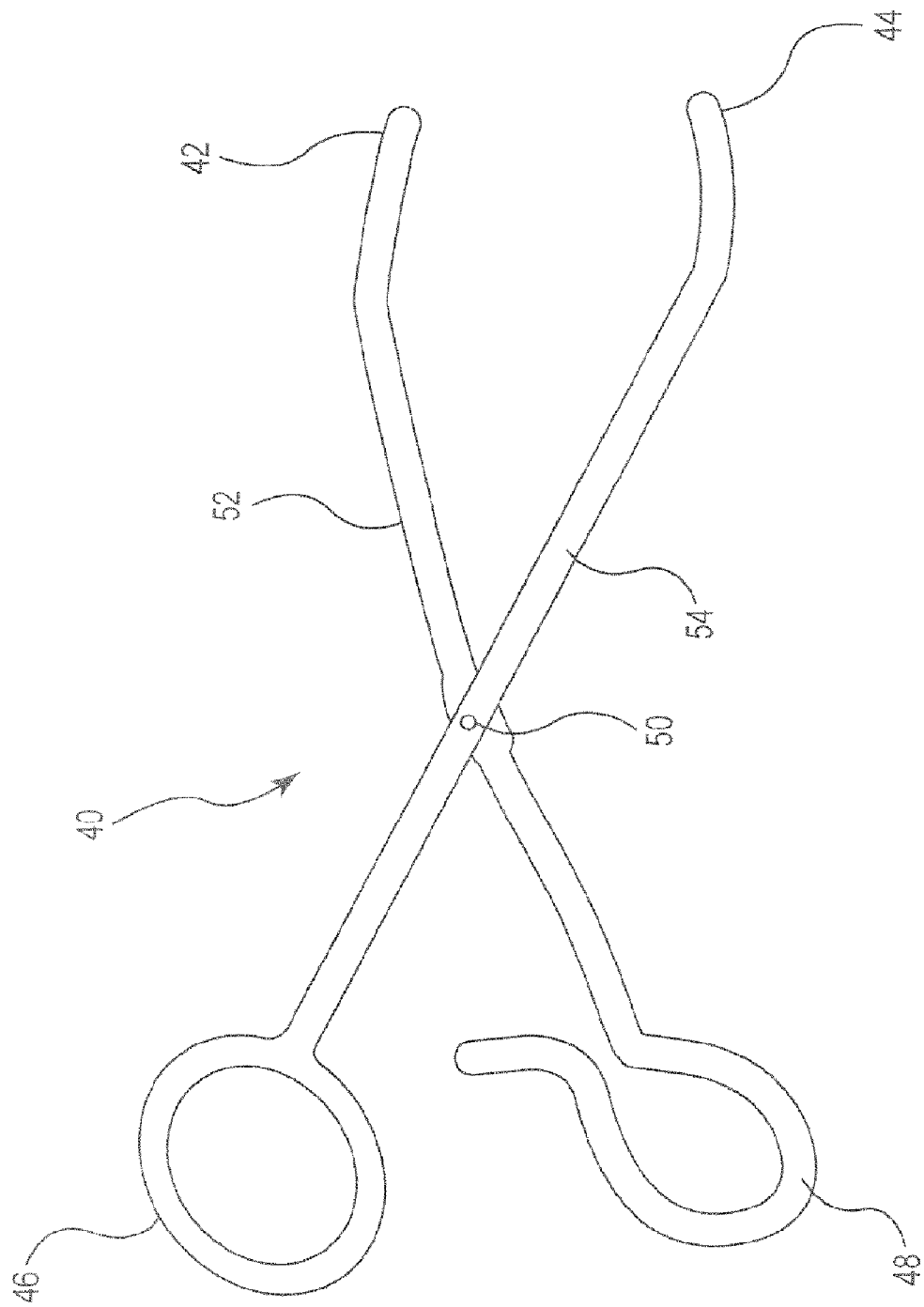
FIG. 11 is a side view of a dilator connection tool.
Figure 12:
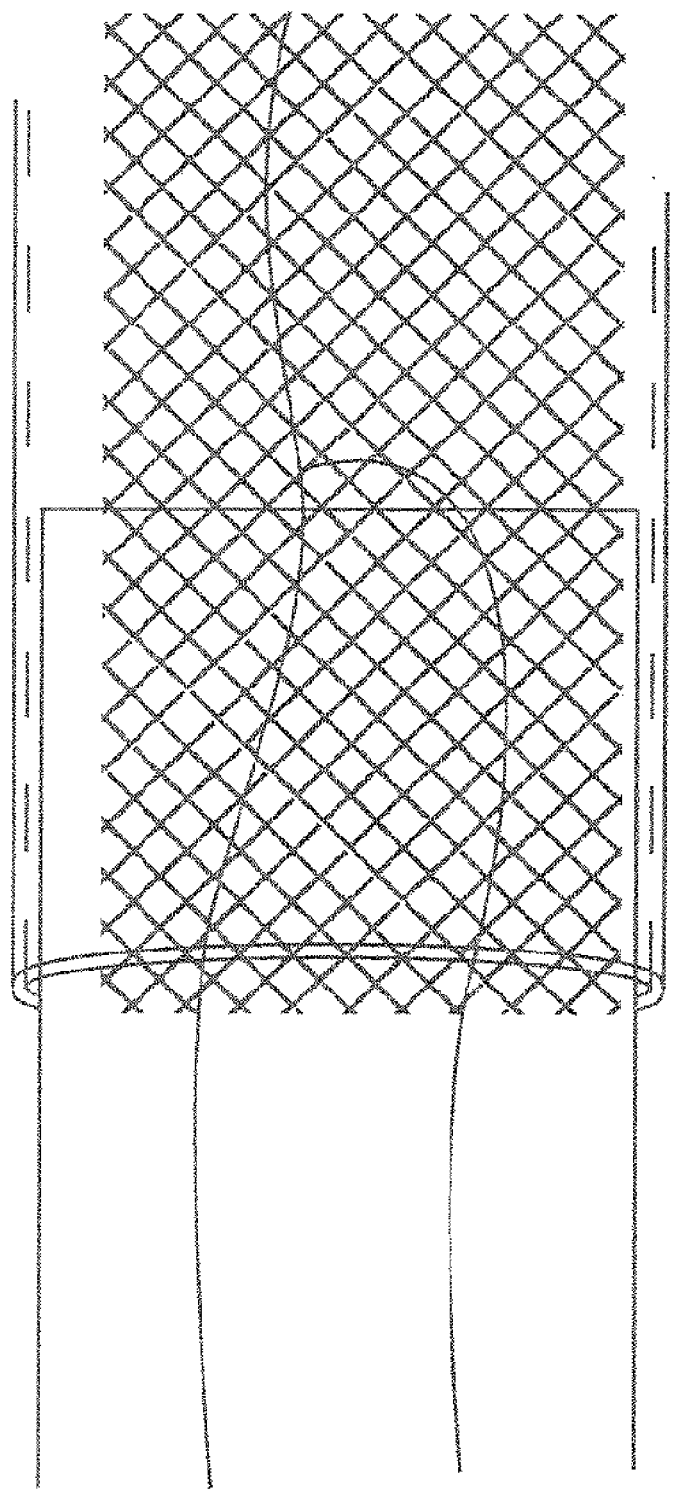
FIG. 12 is a fragmentary view of the support member combined with a sheath.

FIG. 11 discloses a tool 40 for securing dilator 36 onto tip 16 of needle 14. Tool 40 includes a first member 52 rotatably fastened to a second member 54 at a fulcrum 50. First member 52 is generally elongated and includes a first handle 48 at one end and a first support surface 42 at the other end. Similarly, second member 54 is generally elongated and includes a second handle 46 at one end and a second support surface 44 at the other end. In operation, dilator 36 can be supported by first support surface 42 while tip 16 is supported by second support surface 44. As handle 46 is moved closer to handle 48, needle tip 16 is secured to dilator 36, thereby enabling the support structure to be manipulated as the needles 14 are removed from the pelvic tissue.

Figure 18:
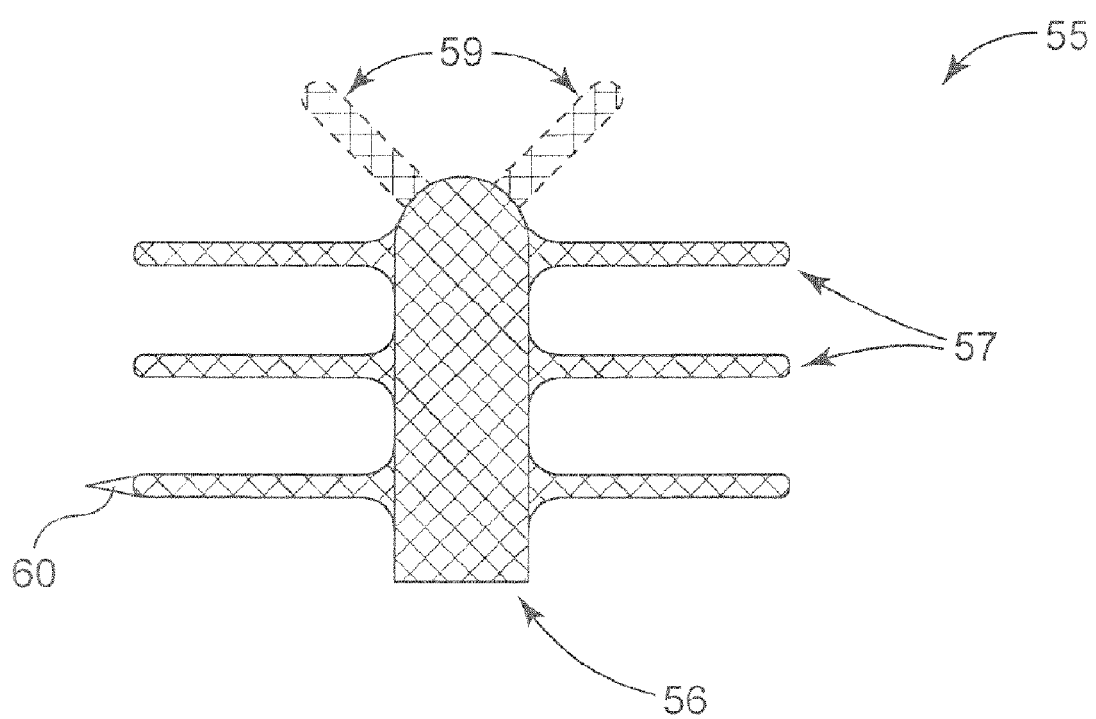
FIG. 18 is a top view of the self-fixating mesh implant of the present invention.

FIG. 18 discloses a self-fixating mesh implant of the present invention. The implant 55 includes a middle portion 56. The implant 55 also includes one or more pairs of legs 57 extending out from the middle portion 56 to the right and left. Posterior legs 59 may extend in a forward and/or rearward direction to provide needed support. The mesh may be fixed without the use of sutures either by relying on the properties of the mesh material itself or by adding a tissue anchor 60 to an end of at least one of the aims of the mesh.

Figure 19:
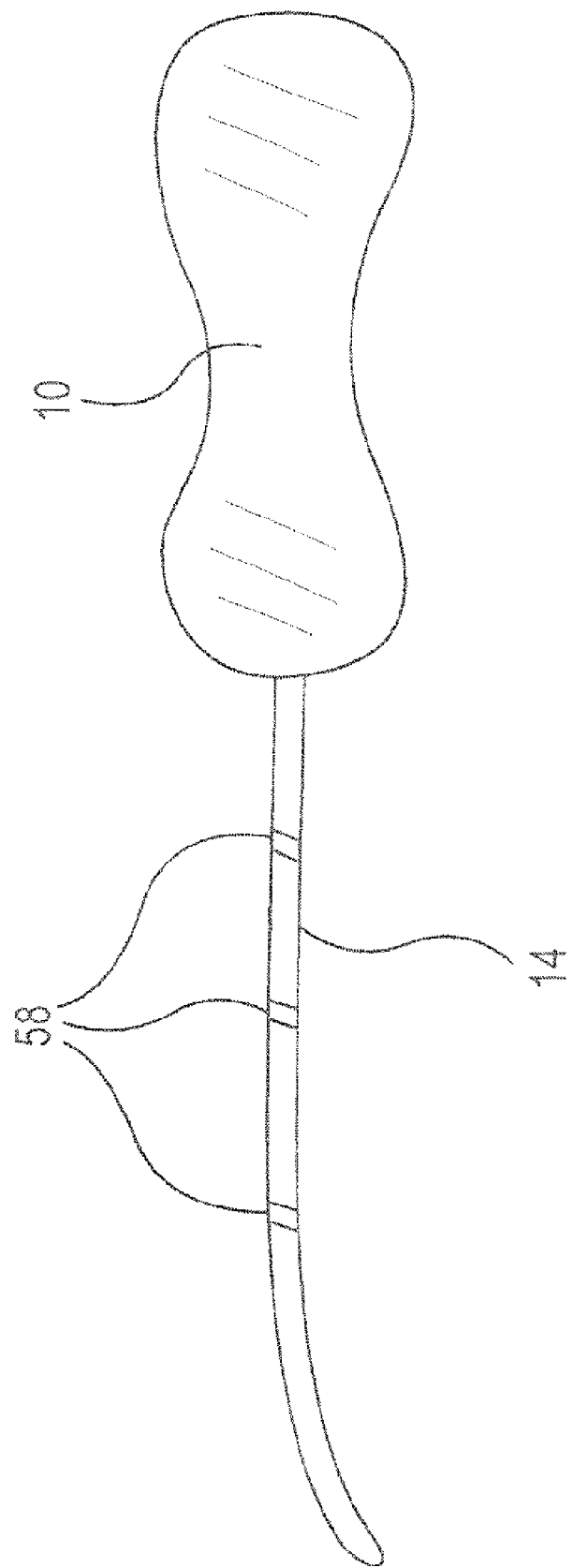
FIG. 19 illustrates a needle with marks for implantation of the self-fixating mesh of the present invention.

FIG. 19 discloses a tool for implanting the self-fixating mesh implant 55 of the present invention. The tool includes a handle 10 and a needle 14. The needle has markings 58 to indicate the depth for implantation of the implant 55, based on the anatomical placement for each leg. The needle tip is optionally adapted to connect to an anchor or dilator to ease placement of the mesh arms.

Numerous modifications and variations of the present invention are possible in light of the above teachings. It is understood that within the scope of the appended claims, the invention may be practiced other than as specifically described herein.

Obviously, numerous modifications and variations of the present invention are possible in light of the above teachings. It is therefore to be understood that within the scope of the appended claims, the invention may be practiced otherwise than as specifically described herein.

Example of Method

While many methods are contemplated herein, an example use of the method and apparatus of treating pelvic organ prolapse is disclosed, referring to FIGS. 12 through 24.

The procedure can be carried out under local or general anesthesia. An incision is made midline across the vaginal apex with sharp and blunt dissection to the ischial spine. Two small incisions are also made in the skin of the buttocks. Needles are passed from perianal skin incisions in the buttocks through the ischial rectal fossa to the vaginal incision.

The needle tip is palpated distal and inferior to the ischial spine prior to passage through the coccygeus muscle. Further dissection may be desired to aid palpation of the needle passage. Connectors are connected to each needle end. Needles are retracted and mesh is positioned. The mesh is then attached to the vaginal vault, and optionally to the lateral perirectal space or perineal body, tensioned, and the incisions are closed.

One embodiment of the present invention is a sterile, single use product consisting of two stainless steel curved needles and a polypropylene mesh implant. The same polypropylene mesh is available in an alternative configuration that allows the attachment of biological material.

Locking connectors on the ends of the mesh attach to each needle tip and are used to hold the mesh secure to the needle during passage of the mesh through the body. The connectors may be removed, if desired.

Four main preferred embodiments of the present apparatus are herein described. The physician may decide at his/her discretion which configuration is most appropriate for a particular patient.

A first embodiment (described herein as the tape embodiment) includes one-piece self-fixating mesh two removable plastic insertion sheaths over the mesh, and two locking connectors attached to the insertion sheaths. The tape is knitted polypropylene monofilament mesh that is pre-cut to 1.1 cm width×50 cm length with a non-absorbable or absorbable tensioning suture (polypropylene) threaded through the length to allow for tensioning adjustment after placement. The sheath affords convenient travel of the mesh through the tissue. Finger loops are formed by the sheath to allow for easy attachment of the connectors to the needle tips. The synthetic mesh tape is intended to remain in the body as a permanent implant.

A second embodiment (described herein as the cape embodiment) adds a 4 cm×13 cm mesh to the tape. This soft knitted mesh has large pores and is also made of polypropylene. The mesh is pre-attached to the tape and can be trimmed to suit surgical preference.

A third embodiment (described herein as the bio-cape embodiment) consists of two separate 1.1 cm×22 cm polypropylene mesh pieces, using the same material as in the tape version. However, one end has a locking connector and finger loop and the other end has a plastic clamp attached to a Y-shaped mesh used to facilitate attachment to a biological implant. The clamp is designed to facilitate the attachment of graft material with sutures.

In order to use the present invention in treatment of pelvic organ prolapse, the patient should initially be prepared by placing the patient in a modified dorsal lithotomy position with hips flexed, legs elevated in stirrups, and buttocks even with the edge of the table. Vaginal retraction may be used, if desired. Palpate the location of the ischial spines.

The fourth main embodiment of the present invention is a self-fixating mesh implant having a middle portion and several pairs of legs extending therefrom, in which the arms are designed to be fixed into supportive tissue by tissue anchors or by the material characteristics of the mesh itself.

The various embodiments require differing product preparations. Generally, the process includes steps to gain access to the target organ. For example, in treatment of posterior vaginal prolapse, the steps may include:

(1) Gaining access to the external vaginal vault using surgeon's preferred method of incision and dissection. If the cape is used, complete rectovaginal dissection may be required.

Figure 13:
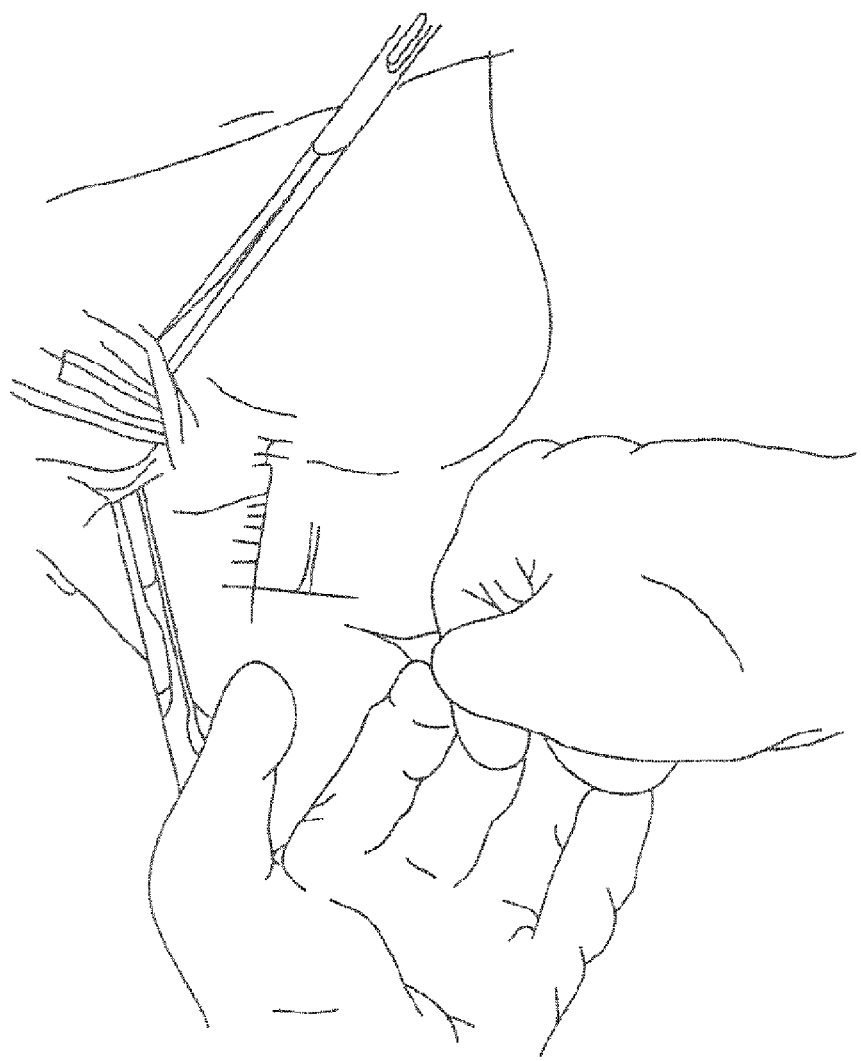
FIG. 13 illustrates the positioning of external incisions on the rectum of the patient.

(2) Making the appropriate incisions. In a preferred method, two small stab incisions are made on each side of the rectum approximately 3 cm lateral and 3 cm posterior to the anus, as shown in FIG. 13.

(3) Grasping the needle in one hand with the needle tip between the thumb and forefinger. Place the other hand near the needle bend. The two needles are identical. Either side may be done first.

Figure 14:
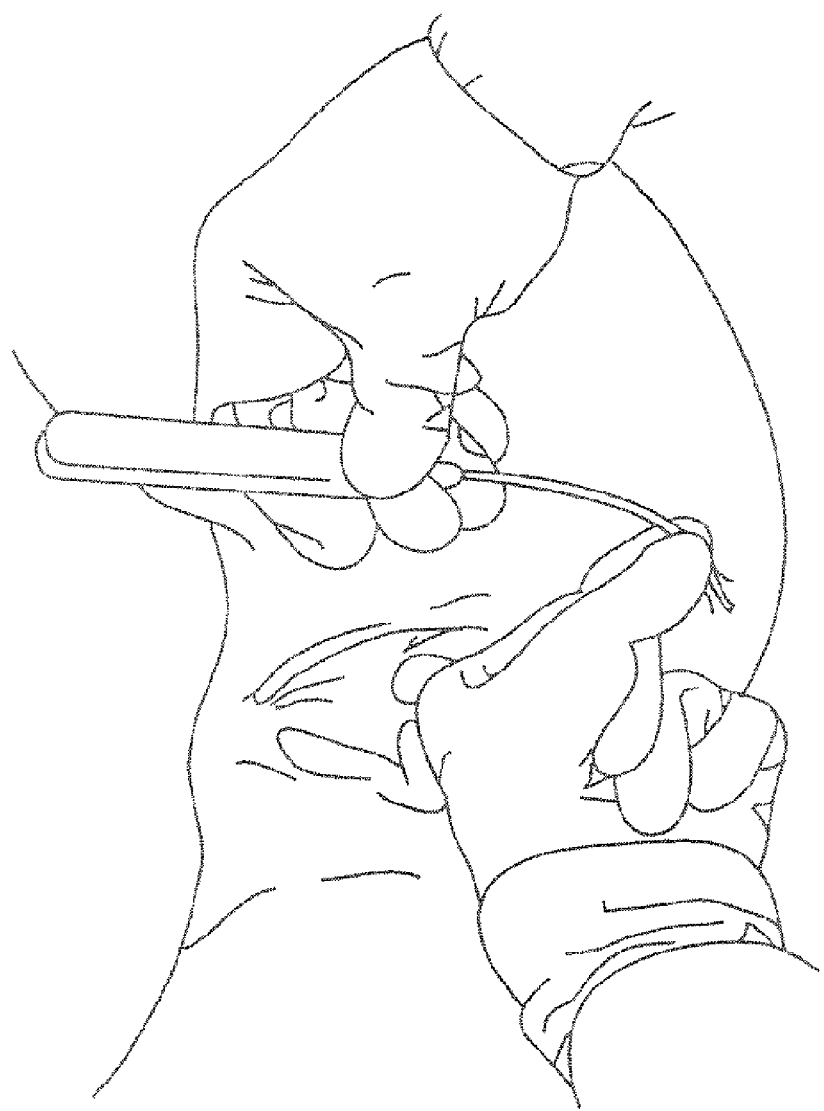
FIG. 14 illustrates a method of inserting the needle in a patient.

(4) Pointing the needle tip perpendicular to the skin with the handle pointing upward in a 12:00 position, as shown in FIG. 14.

(5) Directing the needle at a slight upward and lateral angle through the buttock. Puncture the initial layers of tissue by pushing on the needle bend until the needle enters the ischiorectal fossa.

Figure 15:
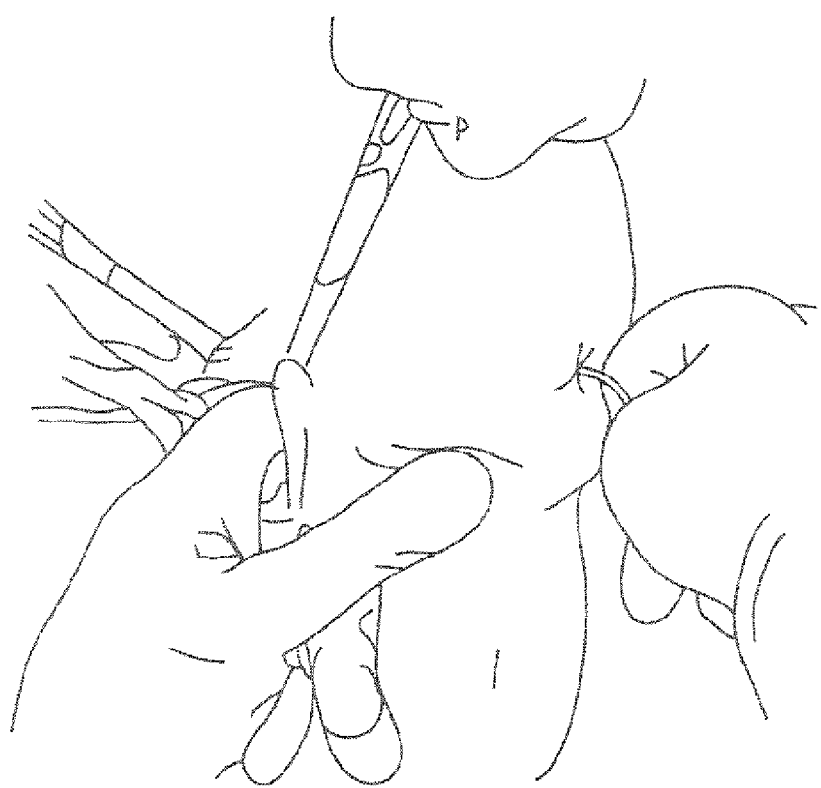
FIG. 15 illustrates palpation to aid passage of the needle to its appropriate position.

(6) Continuing to pass the needle tip lateral and parallel to the rectum toward the ischial spine. Palpate as needed, as shown in FIG. 15.

(7) Palpating the needle tip in front of the ischial spine. Penetrate the levator muscle advancing and lightly turning the needle tip medially toward the vaginal vault.

(8) Performing digital rectal exam to verify rectal integrity.

(9) Repeating steps 3-9 on patient's contralateral side.

Figure 16:
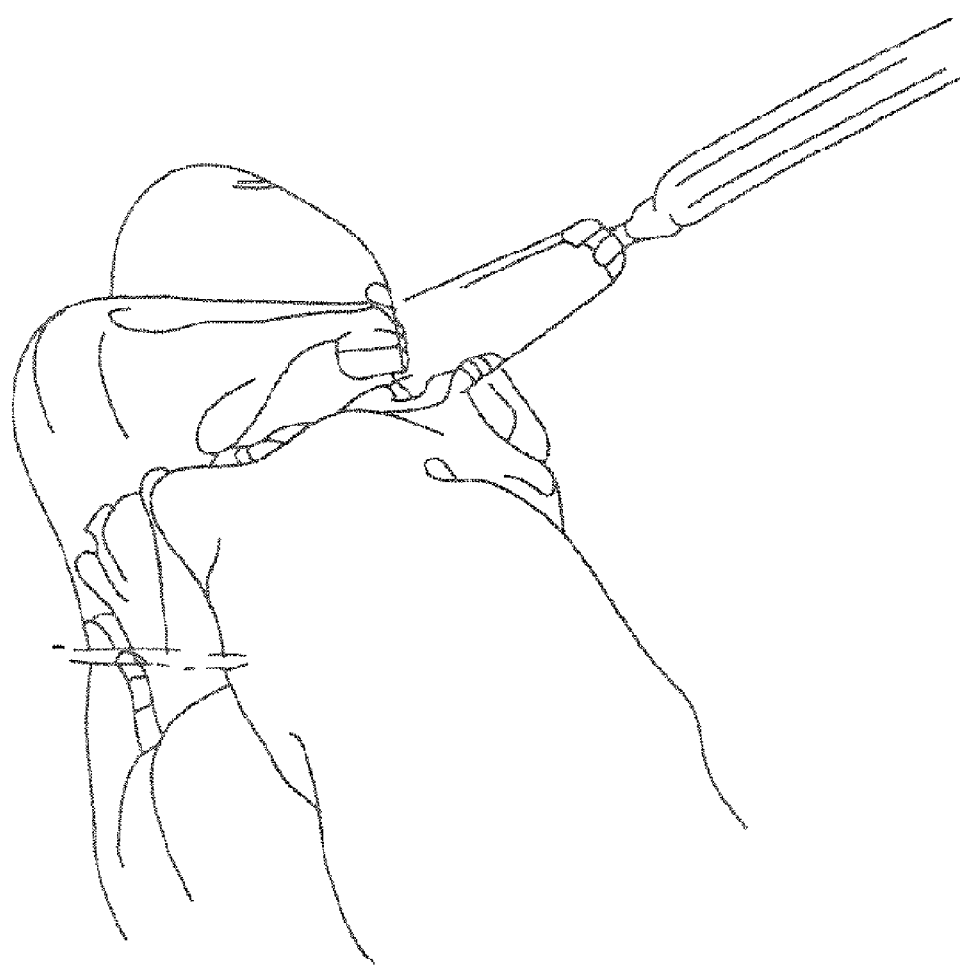
FIG. 16 illustrates an embodiment of the connector on the end portion of the mesh.

(10) Inserting a finger into the loop behind the connector on the mesh, as shown in FIG. 16. Insert the connector into the vagina. Snap onto the needle tip.

(11) Pulling each needle and connector back through the skin incision. Adjust the sheath and mesh into an approximate position.

(12) Cutting the needles from the mesh near the end of the sheath, below the blue dots provided to guide the surgeon.

(13) Attaching the mesh to the exterior apex of the vaginal wall with two or more sutures.

(14) Ensuring the vaginal wall is in the appropriate anatomic position. If the cape is being used, lay the cape in the perirectal space, in a tension-free manner, and close the perirectal fascia over the mesh or the vaginal incision.

Figure 17:
FIG. 17 illustrates positioning of the mesh by manipulating the sheathed end portions.

(15) Pulling on the mesh assemblies to make final adjustments, as shown in FIG. 17.

(16) Removing plastic sheaths.

(17) Trimming the mesh at the level of the subcutaneous tissue.

(18) Closing the incisions.

(19) Using a vaginal pack and antibiotic prophylaxis as appropriate.

As an alternative embodiment, the invention may include a kit, apparatus, and method with only one needle. In these alternative embodiments, it is necessary to:

(1) Gain access to the external vaginal vault using surgeon's preferred method of incision and dissection. If the cape is used, complete rectovaginal dissection is required.

(2) Make two small stab incisions on each side of the rectum approximately 3 cm lateral and 3 cm posterior to the anus, as shown in FIG. 13.

(3) Grasp the needle in one hand with the needle tip between the thumb and forefinger. Place the other hand near the needle bend.

(4) Point the needle tip perpendicular to the skin with the handle pointing upward in a 12:00 position, as shown in FIG. 14.

(5) Direct the needle at a slight upward and lateral angle through the buttock. Puncture the initial layers of tissue by pushing on the needle bend until the needle enters the ischiorectal fossa.

(6) Continue to pass the needle tip lateral and parallel to the rectum toward the ischial spine. Palpate as needed, as shown in FIG. 15.

(7) Palpate the needle tip in front of the ischial spine. Penetrate the levator muscle advancing and lightly turning the needle tip medially toward the vaginal vault.
(8) Perform digital rectal exam to verify rectal integrity.
(9) Repeat steps 3-9 with the single needle on the patient's contralateral side.
(10) Insert a finger into the loop behind the connector on the mesh, as shown in FIG. 16.
(11) Pull the needle and connector back through each skin incision. Adjust the sheath and mesh into an approximate position.
(12) Attach the mesh to the exterior apex of the vaginal wall with two or more sutures.
(13) Ensure the vaginal wall is in the appropriate anatomic position. If the cape is being used, lay the cape in the perirectal space, in a tension-free manner, and close the perirectal fascia over the mesh or the vaginal incision.
(14) Pull on the mesh assemblies to make final adjustments, as shown in FIG. 17.
(15) Remove plastic sheaths.
(16) Trim the mesh at the level of the subcutaneous tissue.
(17) Close the incisions.
(18) Use the vaginal pack and antibiotic prophylaxis as appropriate.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for repair of pelvic organ prolapse in a patient, said method comprising the steps of:
    using a first needle to establish a first pathway in tissue on a first side of said prolapsed organ, said pathway extending between an external perirectal region to a region of an ischial spine of the patient, said first needle comprising a tip, a straight portion, a first radius, and a second radius distinct from the first radius, wherein the first radius and the second radius are located between the straight portion and the tip;
    positioning a support member in a position to reposition said prolapsed organ in said organ's anatomically correct location, said support member comprising a support portion having a first and second end, first end portion, and second end portion, said first end portion and second end portion respectively attached to said first end and said second end;
    connecting said first end portion to the tip of the first needle;
    introducing said first end portion through said first pathway by removing the first needle from the first pathway;
    using a second needle to establish a second pathway in tissue on a contralateral side of said prolapsed organ, said pathway extending between an external perirectal region to a region of an ischial spine of the patient, said second needle comprising a tip, a straight portion, a first radius, and a second radius distinct from the first radius, wherein the first radius and the second radius are located between the straight portion and the tip;
    connecting said second end portion to the tip of the second needle; and,
    introducing said second end portion through said second pathway by removing the second needle from the second pathway,
    adjusting said first end portion and said second end portion so that said support member is in a therapeutic relationship to a tissue of said prolapsed organ that is to be supported;
    wherein said pelvic organ prolapse is a vaginal vault prolapse, and
    wherein the step of using a first needle to establish a first pathway in tissue on a first side le a said prolapsed organ, said pathway extending between an external perirectal region to a region of an ischial spine of the patient, said first needle comprising a tip, a straight portion, a first radius, and a second radius distinct from the first radius, wherein the first radius and the second radius are located between the straight portion and the tip, comprises the steps of:
        making a midline incision in an apex of a vagina;
        dissecting to a region of an ischial spine;
        making a first incision lateral and posterior to the rectum in a skin of a buttock;
        rotating the first needle about the first radius to pass the first needle from said first incision toward said vaginal incision, wherein the second radius is in contact with the vaginal incision;
        palpating a tip of said needle distal and inferior to an ischial spine; and
        passing said needle through a coccygeous muscle.

2. The method of claim 1, wherein the step of connecting said first end portion to the tip of the first needle comprises the step of pressing the first end portion to the tip of the first needle using a fastening tool.

3. The method of claim 1 wherein the step of using a second needle to establish a second pathway in tissue on a contralateral side of said prolapsed organ, said pathway extending between an external perirectal region to a region of an ischial spine of the patient, comprises the steps of:
    making a second incision lateral and posterior to the rectum in a skin of a buttock on the contralateral side respective to said first incision;
    rotating the second needle about a first radius to pass the second needle from said second incision toward said vaginal incision;
    palpating a tip of said second needle distal and inferior to an ischial spine; and
    passing said needle through a coccygeous muscle.

4. The method of claim 1 wherein said step of introducing said first end portion through said first pathway by removing the first needle from the first pathway, comprises the step of removing said first needle from an incision in said patient's external perirectal region through a tissue on a side of said prolapsed organ through to said region of an ischial spine of the patient to form said first pathway.

5. The method of claim 1, wherein said step of introducing said second end portion through said second pathway by removing the second needle from the second pathway comprises the step of retracting back through said second pathway a second needle to which said second end portion has been connected.

6. The method of claim 1, wherein said step of adjusting said end portions so that said support member is in a therapeutic relationship to a tissue of said prolapsed organ that is to be supported further comprises:
    attaching said support member to a vaginal wall with sutures;
    ensuring a vaginal vault is in an appropriate anatomical position; and adjusting said support member by manipulation of said end portions.

7. The method of claim 1 wherein the first radius of curvature of the first needle is between the tip of the first needle and the second radius of curvature of the first needle, and the first radius of curvature of the first needle is between about 2 inches and about 4 inches and the second radius of curvature of the first needle is between about 4 inches and about 6 inches.

8. The method of claim 7, wherein the straight section of the first needle is between about 3 inches and about 7 inches.

9. The method of claim 8, wherein the straight section of the first needle is between about 5.5 inches and about 6.5 inches.

10. The method of claim 7 wherein the first radius of curvature of the second needle is between the tip of the second needle and the second radius of curvature of the second needle, and the first radius of curvature of the second needle is between about 2 inches and about 4 inches and the second radius of curvature of the second needle is between about 4 inches and about 6 inches.

11. The method of claim 10, wherein the straight section of the second needle is between about 3 inches and about 7 inches.

12. The method of claim 11, wherein the straight section of the second needle is between about 5.5 inches and about 6.5 inches.

13. The method of claim 1 wherein the support member comprises self-fixating supporting mesh, and a mesh knit of an end portion is different from a mesh knit of the support portion.

14. The method of claim 1, wherein the support portion comprises first and second sides located opposite one another, a first end and a second end opposite one another and located between the two sides, and a first pair of end portions extending from a portion of the sides proximate the first end and a second pair of end portions extending from a portion of the sides proximate the second end.

15. The method of claim 14, comprising a third pair of end portions extending from the sides of the support portion between the first and second pairs of end portions.

16. A method for repair of pelvic organ prolapse in a patient, said method comprising the steps of:
using a first needle to establish a first pathway in tissue on a first side of said prolapsed organ, said pathway extending between an external perirectal region to a region of an ischial spine of the patient, said first needle comprising a tip, a straight portion, a first radius, and a second radius distinct from the first radius, wherein the first radius and the second radius are located between the straight portion and the tip;
positioning a support member in a position to reposition said prolapsed organ in said organ's anatomically correct location, said support member comprising a support portion having a first and second end, first end portion, and second end portion, said first end portion and second end portion respectively attached to said first end and said second end;
connecting said first end portion to the tip of the first needle;
introducing said first end portion through said first pathway by removing the first needle from the first pathway;
using a second needle to establish a second pathway in tissue on a contralateral side of said prolapsed organ, said pathway extending between an external perirectal region to a region of an ischial spine of the patient, said second needle comprising a tip, a straight portion, a first radius, and a second radius distinct from the first radius, wherein the first radius and the second radius are located between the straight portion and the tip;
connecting said second end portion to the tip of the second needle;
introducing said second end portion through said second pathway by removing the second needle from the second pathway; and
adjusting said first end portion and said second end portion so that said support member is in a therapeutic relationship to a tissue of said prolapsed organ that is to be supported;
wherein the first radius of curvature of the first needle is between the tip of the first needle and the second radius of curvature of the first needle, and the first radius of curvature of the first needle is between about 2 inches and about 4 inches and the second radius of curvature of the first needle is between about 4 inches and about 6 inches.

17. The method of claim 16, wherein the straight section of the first needle is between about 3 inches and about 7 inches.

18. The method of claim 17, wherein the straight section of the first needle is between about 5.5 inches and about 6.5 inches.

19. The method of claim 16 wherein the first radius of curvature of the second needle is between the tip of the second needle and the second radius of curvature of the second needle, and the first radius of curvature of the second needle is between about 2 inches and about 4 inches and the second radius of curvature of the second needle is between about 4 inches and about 6 inches.

20. The method of claim 16, wherein the straight section of the second needle is between about 3 inches and about 7 inches.

21. The method of claim 16, wherein the straight section of the second needle is between about 5.5 inches and about 6.5 inches.

* * * * *

UNITED STATES PATENT AND TRADEMARK OFFICE
CERTIFICATE OF CORRECTION

PATENT NO. : 8,206,281 B2  
APPLICATION NO. : 12/855792  
DATED : June 26, 2012  
INVENTOR(S) : Kimberly A. Anderson and James E. Cox Page 1 of 1

It is certified that error appears in the above-identified patent and that said Letters Patent is hereby corrected as shown below:

On the Title Page

Page 3, column 1, Item 56 under FOREIGN PATENT DOCUMENTS, "EP 1 093 768" should be -- EP 1 093 758 --.

Page 4, column 1, Item 56 under OTHER PUBLICATIONS, under Karram, Mickey, "Lala" should be -- Lata --; under Kovac, S. Robert, "Sting" should be -- Sling --.

Page 5, column 1, Item 56 under OTHER PUBLICATIONS, under Petros, P.E. Papa, et al., "Ural" should be -- Urol --; under Petros, P.E. Papa, et al., "Blomechanics" should be -- Biomechanics --; column 2, under Stanton, Stuart L., "PRCOG" should be -- FRCOG --.

Page 6, column 2, Item 56 under OTHER PUBLICATIONS, under Hernlarnesh USA Inc., "Jan, 2001" should be -- Jan. 2000 --.

In the Specification

Column 9, line 11, "14 lines" should be -- 14 lies --.

Signed and Sealed this  
Twentieth Day of May, 2014

Michelle K. Lee  
*Deputy Director of the United States Patent and Trademark Office*